(12) United States Patent
Bourne

(10) Patent No.: US 11,350,903 B2
(45) Date of Patent: Jun. 7, 2022

(54) RADIATION DETECTION SYSTEM

(71) Applicant: Elekta Limited, Crawley (GB)

(72) Inventor: Duncan Bourne, Sussex (GB)

(73) Assignee: Elekta Limited, Crawley (GB)

( * ) Notice: Subject to any disclaimer, the term of this patent is extended or adjusted under 35 U.S.C. 154(b) by 0 days.

(21) Appl. No.: 15/733,632

(22) PCT Filed: Mar. 26, 2019

(86) PCT No.: PCT/EP2019/057646
§ 371 (c)(1),
(2) Date: Sep. 21, 2020

(87) PCT Pub. No.: WO2019/185665
PCT Pub. Date: Oct. 3, 2019

(65) Prior Publication Data
US 2021/0015441 A1    Jan. 21, 2021

(30) Foreign Application Priority Data

Mar. 27, 2018 (GB) ..................... 1804918

(51) Int. Cl.
*G01N 23/04* (2018.01)
*A61B 6/00* (2006.01)
*A61N 5/10* (2006.01)
*G01T 1/20* (2006.01)

(52) U.S. Cl.
CPC .............. *A61B 6/54* (2013.01); *A61B 6/4208* (2013.01); *A61B 6/4266* (2013.01); *A61N 5/1045* (2013.01); *G01T 1/20* (2013.01)

(58) Field of Classification Search
CPC ....... A61B 6/54; A61B 6/4208; A61B 6/4266; G01T 1/20; A61N 5/1045
See application file for complete search history.

(56) References Cited

U.S. PATENT DOCUMENTS

| | | | |
|---|---|---|---|
| 5,712,890 | A | 1/1998 | Spivey et al. |
| 6,038,286 | A | 3/2000 | Waegli et al. |
| 2006/0227934 | A1 | 10/2006 | Beckhaus et al. |
| 2009/0196399 | A1 | 8/2009 | Schmitt et al. |
| 2009/0283682 | A1 | 11/2009 | Star-lack et al. |
| 2010/0006767 | A1 | 1/2010 | Enomoto |
| 2015/0316661 | A1* | 11/2015 | Fujiyoshi .............. G01T 1/2018 378/62 |

(Continued)

FOREIGN PATENT DOCUMENTS

| | | |
|---|---|---|
| WO | WO-2010136911 A1 | 12/2010 |
| WO | WO-2017178300 A1 | 10/2017 |

OTHER PUBLICATIONS

"International Application Serial No. PCT/EP2019/057646, International Search Report dated Jul. 2, 2019", (dated Jul. 2, 2019), 3 pgs.

(Continued)

*Primary Examiner* — Kiho Kim
(74) *Attorney, Agent, or Firm* — Schwegman Lundberg & Woessner, P.A.

(57) ABSTRACT

There is provided a radiation detection system for a radiotherapy device comprising: a plurality of detectors moveable to position each detector in turn in an imaging position to detect radiation.

20 Claims, 16 Drawing Sheets

(56) References Cited

U.S. PATENT DOCUMENTS

2015/0378047 A1* 12/2015 Chen .................... G01V 5/005
                                                    378/5
2018/0078784 A1*  3/2018 Schnarr ............... A61N 5/1031
2018/0345042 A1* 12/2018 Voronenko .......... A61N 5/1045

OTHER PUBLICATIONS

"International Application Serial No. PCT/EP2019/057646, Written Opinion dated Jul. 2, 2019", (dated Jul. 2, 2019), 6 pgs.
"European Application Serial No. 1804918.9, European Search Report dated Sep. 6, 2018", (Sep. 6, 2018), 9 pgs.

* cited by examiner

RADIATION DETECTION SYSTEM

PRIORITY APPLICATIONS

This application is a U.S. National Stage Filing under 35 U.S.C. § 371 from International Application No. PCT/EP2019/057646, filed on Mar. 26, 2019, and published as WO2019/185665 on Oct. 3, 2019, which claims the benefit of priority to Great Britain Application No. 1804918.9, filed on Mar. 27, 2019, 2018; the benefit of priority of each of which is hereby claimed herein, and which applications and publication are hereby incorporated herein by reference in their entireties.

FIELD

The present disclosure relates to a radiation detection system, a radiation detection system suitable for a radiotherapy device, and to a radiotherapy device comprising a radiation detection system.

BACKGROUND

Radiotherapy uses high-energy X-rays to destroy cancerous tissue within the body. Within radiotherapy, radiation detection systems (e.g. imagers) are used for several different purposes. As a means of positioning the patient, it is common to acquire X-ray images of the patient prior to treatment to ensure they have been set up in the correct position. As a means of assessing the radiation dose imparted to the patient, it is common practice to use portal imaging devices to measure the intensity of the radiation after it has passed through the patient, showing the shape of the radiation beam at any given time during the treatment.

Known radiation detection systems include: X-ray sensitive film which can provide a stationary image of the subject; a scintillator used to convert X-rays into light and a mirror to direct the light towards an optical camera to create an image representing the X-rays received at the scintillator; and Electronic Portal Imaging Devices (known as EPIDs), which use large area solid state detectors such as Charge-Coupled Detectors (CCDs) detectors.

Multi-leaf collimators are used to shape the beam of treatment radiation. Radiation detection systems are used to determine the position of the leaves within the multi-leaf collimator, to determine the shape of the collimated beam.

Radiation detection systems can also be used to directly image the patient's and the patient's position.

Components in a radiotherapy device are exposed to high levels of radiation. Components may be exposed to direct radiation from a source (a target or a scintillator) and also are exposed to scattered radiation. This can be damaging to imaging devices such as cameras.

SUMMARY

Aspects and features of the present invention are described in the accompanying claims.

BRIEF DESCRIPTION OF THE DRAWINGS

Specific embodiments are described below by way of example only and with reference to the accompanying drawings in which:

FIG. 14b illustrates a carousel used in the imager of FIG. 14a.

OVERVIEW

The present invention relates to a radiation detection system for a radiotherapy device. The radiation detection system includes a plurality of detectors moveable to position each detector in turn in an imaging position to image a source. The radiation detection system can use a plurality of detectors formed in either a carousel, belt or bank of detectors to image the source. The movement of the plurality of detectors can be triggered by a command received by the radiation detection system. This command can be triggered several different ways. For example, the movement may be triggered by a predetermined time interval, by receiving a predetermined amount of radiation, by a deterioration in the image quality or voluntarily by input from a person.

The source could be any source of light or other radiation, such as: imaging or treatment radiation; scintillated light from a scintillator; light fluoresced or reflected from a marker on the leaf of a multi-leaf collimator; or a patient in the radiotherapy device.

SPECIFIC DESCRIPTION OF CERTAIN EXAMPLE EMBODIMENTS

Figure 1A:
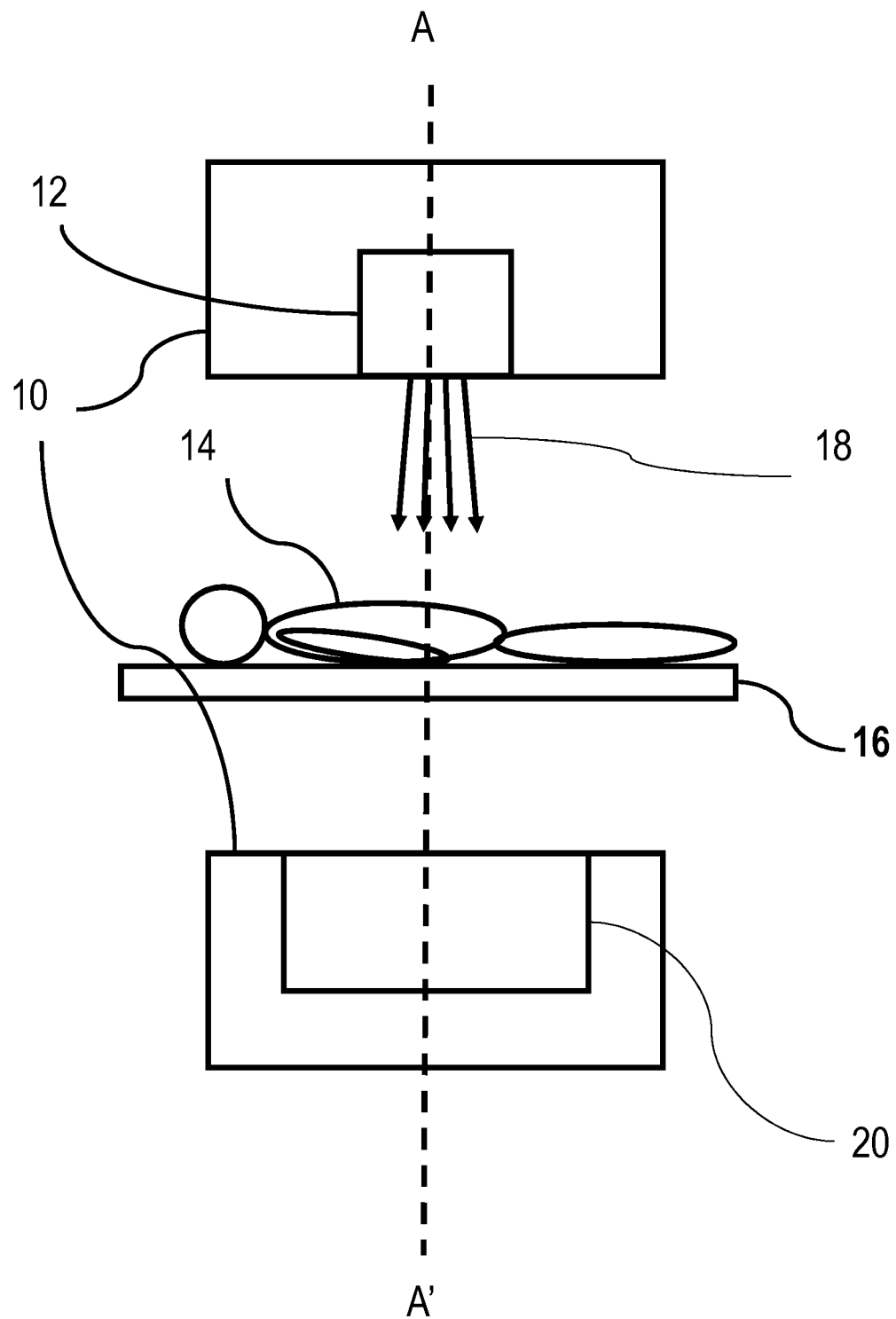
FIGS. 1a and 1b illustrate a known radiotherapy device.
Figure 1B:
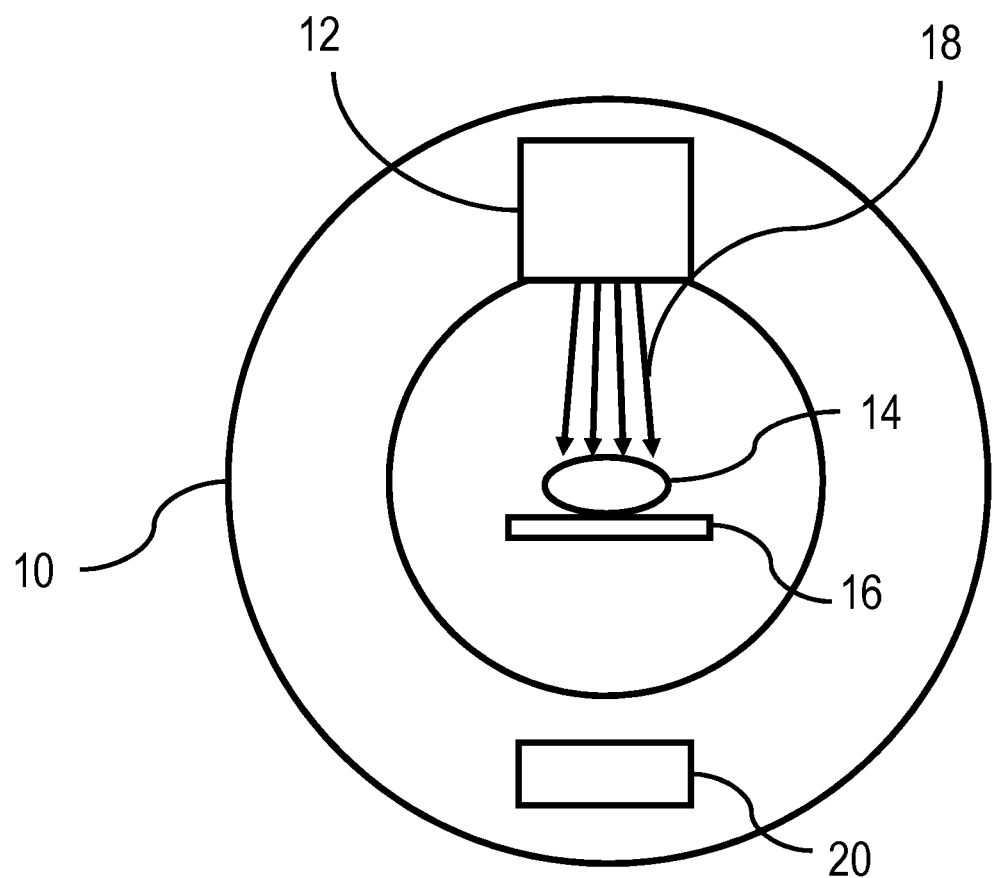

FIG. 1a shows a known radiotherapy device. FIG. 1b is a cut-through of FIG. 1a along line AA'. The radiotherapy device has a gantry 10 and a radiation source 12. A patient 14 lies on a patient support 16 to be treated. A radiation detection system 20 is positioned below the patient support in the gantry. X-rays 18 leave the radiation source 12 and pass through the patient 14 and the patient support 16. The X-rays 18 can be treatment X-rays to treat a tumour in a patient or can be imaging X-rays to image a patient. The X-rays will strike the radiation detection system 20, and a portion of the X-rays are imaged for dosage and/or positioning information. In some radiotherapy devices, the source 12 and radiation detection system 20 are held on arms and are rotatable around the gantry 10 to treat a tumour in the patient with radiation whilst minimising the dose of radiation applied to healthy tissue. The radiation detection system 20 rotates with the source 12 to remain on the opposite side of the patient 14 to the source. Radiation detection systems can also be used in radiotherapy devices which are not rotatable, and which can only provide imaging and/or treatment radiation.

The radiation emitted by the source in the radiotherapy device described in the embodiments throughout this description emit X-rays which are used to image the patient. However, in other embodiments, the radiation used may be, for example, gamma rays, and a scintillator may be used, such as a gamma ray scintillator. Other types of radiation may additionally be envisaged.

PRIOR ART

Figure 2:
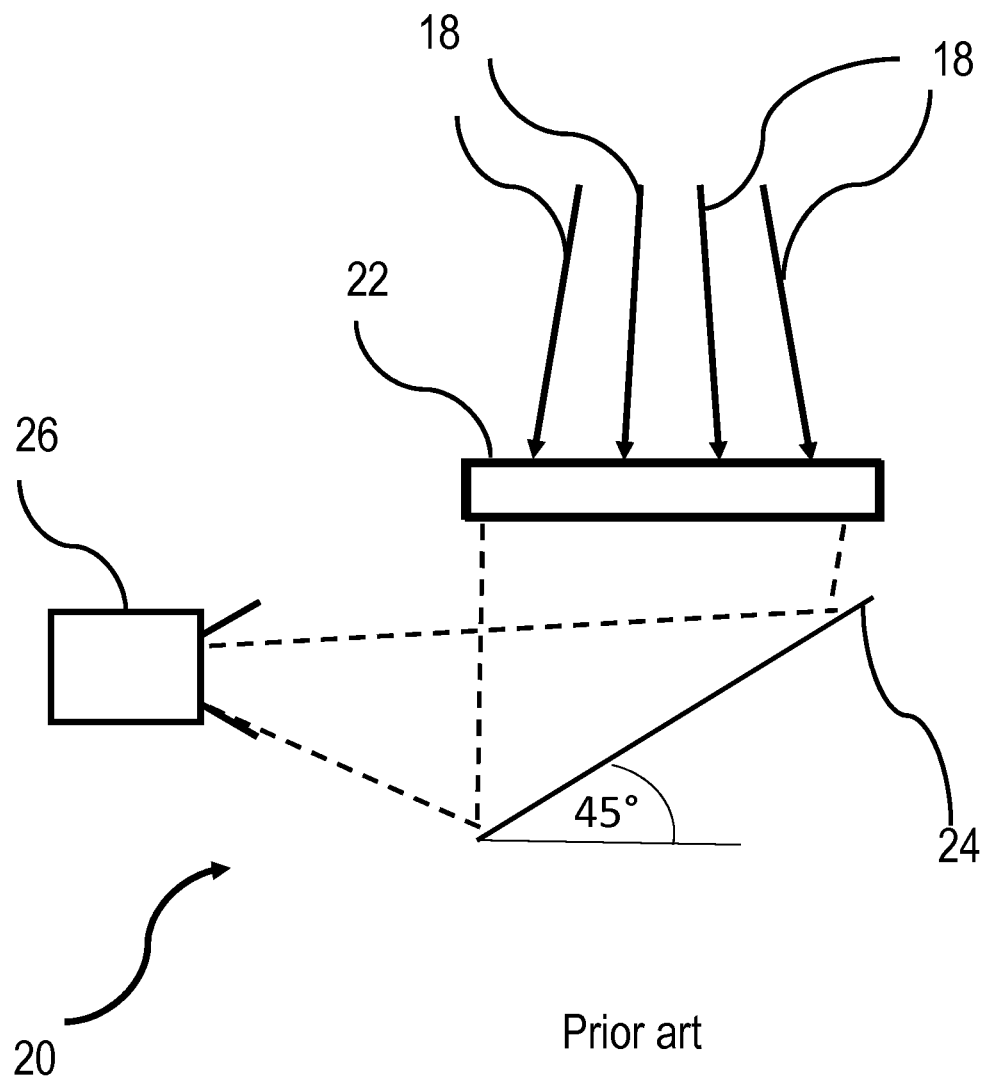
FIG. 2 illustrates a known X-ray radiation detection system.

An example of an X-ray radiation detection system known in the art is shown in FIG. 2. The X-ray radiation detection system 20 includes a scintillator 22, a planar mirror 24 and a detector 26. The mirror is angled at 45 degrees to the plane of the scintillator. The X-ray radiation detection system can be used in the radiation device of FIGS. 1a and 1b. When used in a radiation device, X-rays 18 travel towards an upper face of the scintillator 22 and a portion are converted (i.e. scintillated) into visible light (not shown). The light is emitted in all directions from the scintillator. The majority of the X-rays are not converted into light and pass through the scintillator.

The detector 26 is focussed on the scintillator 22, enabling it to detect light which is emitted from a lower face of the scintillator 22. The detector creates an image of the scintillated light and by extension of the X-rays received at the scintillator. The portion of the scintillator which is imaged by the detector is the imaging area. The detector is a digital camera and providing it has a high enough refresh rate it can create moving video images of the X-rays received at the scintillator. The images can be used to determine how the position of the patient and/or the dose of radiation given to the patient changes during the course of the treatment.

X-rays have a shorter wavelength and therefore a higher energy than visible light. The X-rays can cause damage to components of the detector. Radiation causes damage to detectors gradually when the materials in the detector absorb incident radiation. The detectors receive a cumulative dose when located in a radiation environment, the greater amount of radiation they receive the more likely they are to fail to perform as required. For example, it is common for the contrast in the image to be affected and for electronic systems to fail. Typically, radiation resistant detectors to be used in a radiation environment. These detectors are more expensive than normal detectors as they are built from expensive materials. However, these types of detectors do not produce high quality images. Cheaper detectors typically produce better quality images but break much faster when exposed to radiation.

It is possible for some components of the detectors recover when not exposed to radiation for prolonged period of time. Periods of time spent without exposure to radiation let the materials in the camera anneal and recover from the damage caused by radiation. This helps to increase the lifetime of the cameras.

To protect the detector, it is custom to position the detector outside the path of the X-rays passing through the scintillator. The mirror 24 is positioned in the path of the X-rays so that the detector 26, focussed on the mirror, can view visible light emitted from the scintillator. A standard mirror is used which will reflect light but will not reflect X-rays, which pass through the mirror. The detector 26 is placed at sufficient distance from the mirror 24 so that, with the appropriate lensing, it can view all of the imaging area of the scintillator 22 in the reflection of the mirror. With the mirror angled at 45 degrees, the detector can be placed facing along a plane parallel to the plane of the scintillator.

Carousel

Figure 3:
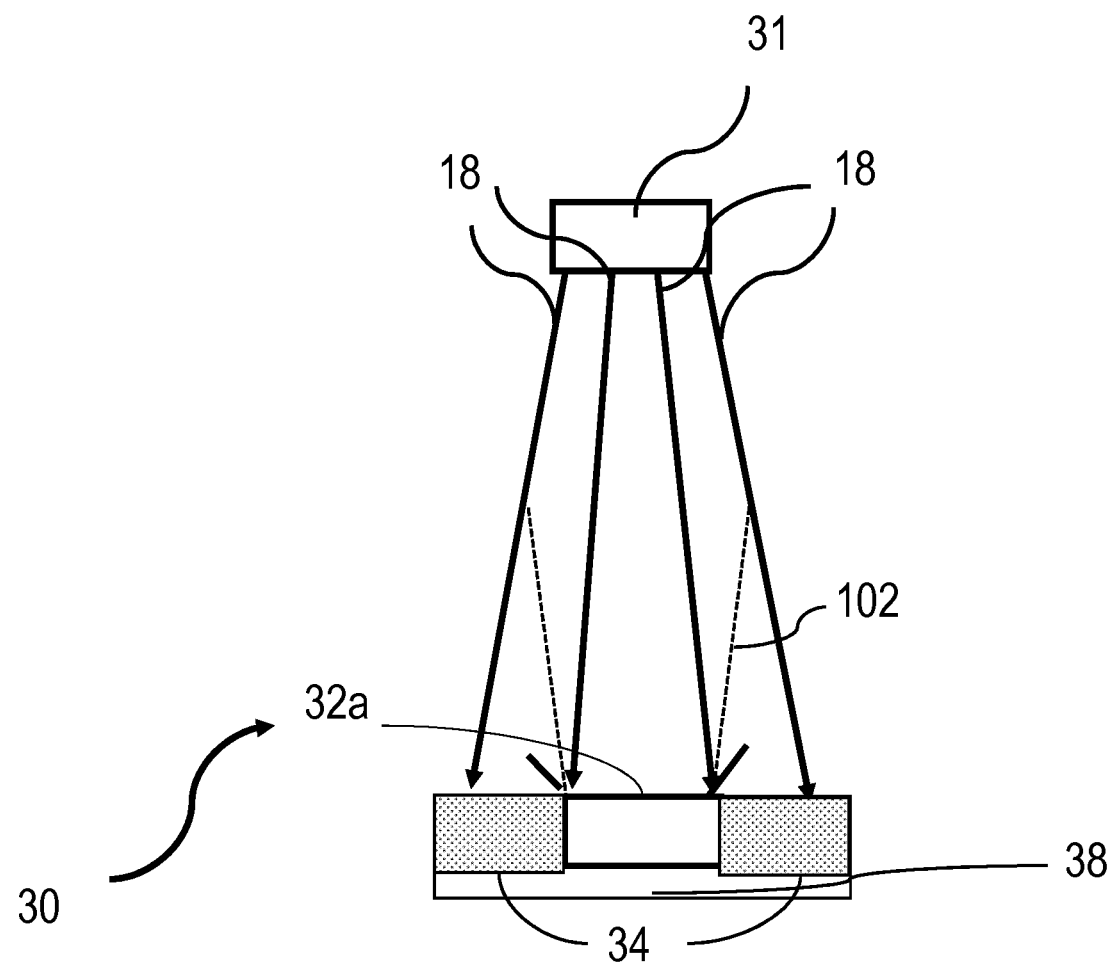
FIG. 3 illustrates a radiation detection system according to a first aspect of the present disclosure.

FIG. 3 shows a radiation detection system according to a first aspect of the present disclosure. The radiation detection system has a plurality of detectors including detector 32a and a carousel 38. The carousel 38 is shown from above in FIGS. 4a and 4b.

Detector 32a is positioned below a source 31 to directly image light or radiation (e.g. X-rays) 18 emitted from the source 31. The field of view of the light or radiation 18 detected and imaged by the detector 32a is shown by dotted lines 102. The detector 32a is positioned in an imaging position in the light or radiation path 18.

In FIG. 3, the source of radiation 18 is shown to be diverging, such as a radiation source such as X-rays emitted from a target. However, the source could be any source of light or other radiation, such as: imaging or treatment radiation; scintillated light from a scintillator; light reflected from a mirror, light fluoresced or reflected from a marker on the leaf of a multi-leaf collimator; or a patient in the radiotherapy device.

Figure 4A:
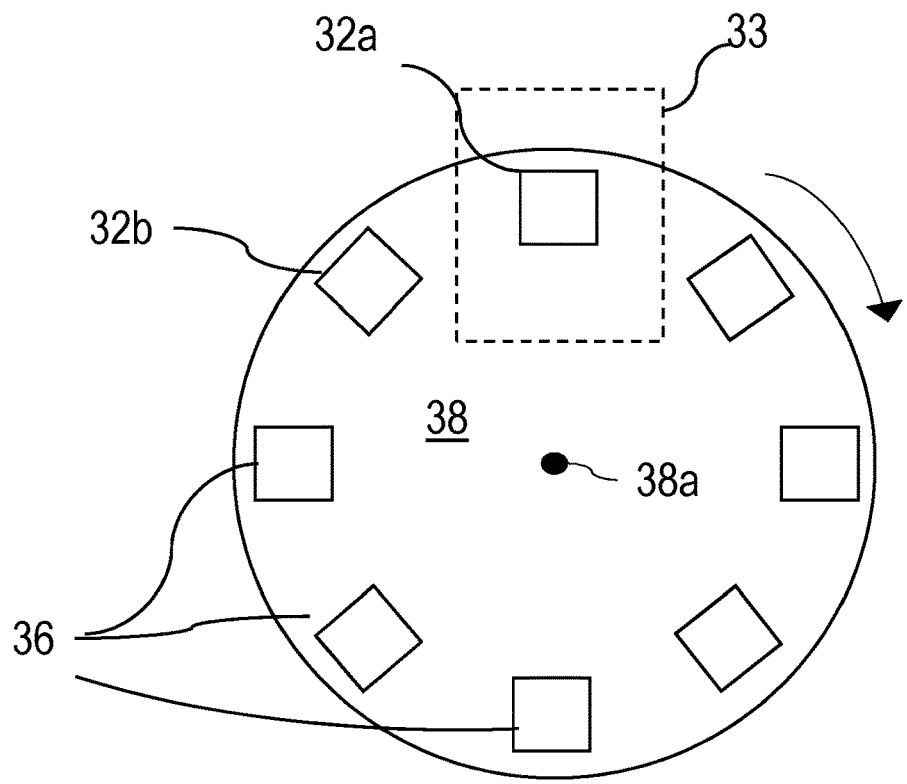
FIGS. 4a and 4b illustrate a carousel used in the radiation detection system of FIG. 3.
Figure 4B:
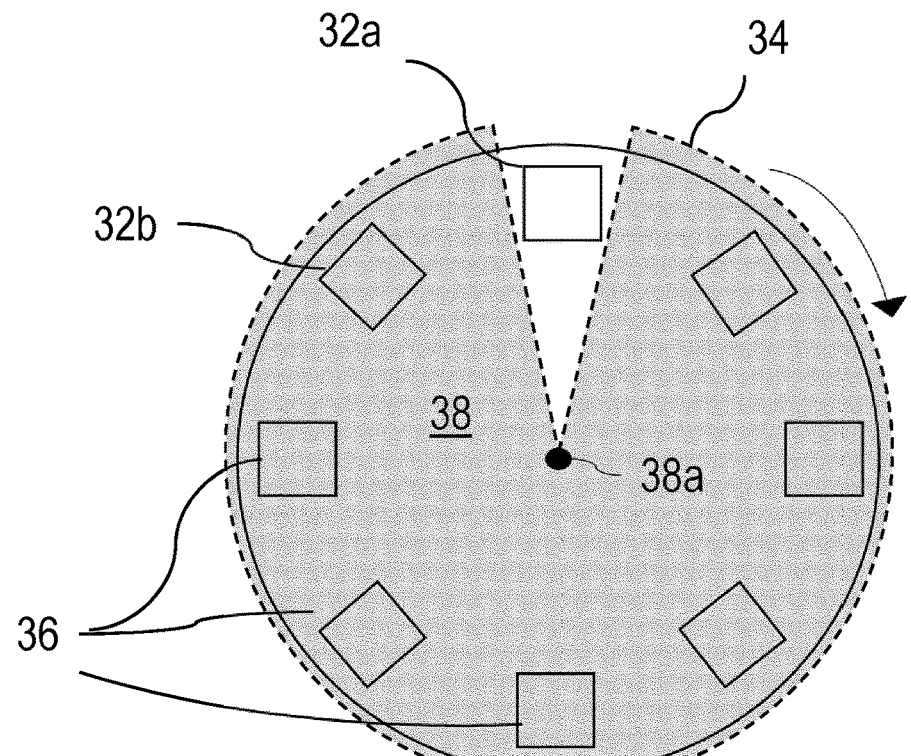

The carousel 38 houses the plurality of detectors 36, including a first detector 32a and a second detector 32b. The carousel is rotatable about an axis 38a. Detector 32a is positioned in the imaging position. The imaging position is in the light or radiation path 18. In this position the detector 36a can image light or radiation emitted from the source 31. The remaining detectors 36 that are not in the imaging position are positioned outside of the light or radiation path 18. The detector in imaging position will experience damage from radiation (for example X-rays), and the detectors outside the radiation path are exposed to a small amount of scattered radiation. The cross section of the path of the direct radiation is shown in FIG. 4a as the dashed line 33. As the remaining detectors are not in the path of direct radiation they will not receive radiation and therefore not experience the same level of damage.

A radiation shield 34 can be placed above the detectors not in the imaging position to help shield them from scattered radiation. The radiation shield 34 is configured to block the source from reaching detectors which are not in the imaging position. The radiation shield 34 may be used in addition to positioning the detectors (other than the detector in the imaging position) out of the line of the cross section of the direct radiation path 33 to shield them from scattered radiation. Alternatively, all the detectors may be in the path of the radiation, and the shield is used to block the radiation from reaching the detectors 36 which are not in the imaging position.

The shield 34 may have a hole overlaying the imaging position, wherein the hole is configured to allow the radiation or light 18 to reach the detector in the imaging position to directly image the source. The hole is located directly over the imaging position. The hole may extend to the edge of the shield. Alternatively, the hole may be in the centre of the shield such that the hole does not extend to the edge of the shield. The shield 34 is made from a high density material. Typically, the higher the density of material used the less thickness you need to absorb the radiation. Good materials for radiation shielding include cast iron, lead and tungsten.

The detector 32a images the source 31 from which light or radiation is emitted. The detector 32a will deteriorate through exposure to the radiation (for example X-rays) as it is sitting in the direct path of the radiation. The detectors also deteriorate from exposure to scattered radiation reflected from surfaces of the radiotherapy device. When the detector has deteriorated beyond use or to a low quality, the plurality of detectors can move the detector 32a out of the imaging position and move the adjacent detector 32b into the imaging position. For example, a carousel 38 can be rotated about axis 38a as shown by the arrow in FIG. 4b. Detector 32b will not have previously been positioned in the cross section of the direct radiation path 33 (or will have been previously located behind a shield) and therefore will not have experienced the level of deterioration of detector 32a, and will be useable to image light or radiation emitted from the source 31. Detector 32b can then be used to image the source 31 until it too deteriorates due to exposure to the radiation. This deterioration may happen over the course of a number of patient treatments.

The movement of the plurality of detectors (e.g. rotation of the carousel 38) can be triggered by a command received by the radiation detection system. When the radiation detection system receives the command, the first detector 32a is moved out of the imaging position and a second detectors 32b is moved into the imaging position. This process happens repeatedly. The command may be triggered by a predetermined time interval, for example when a detector has been in the imaging position for a predetermined amount of time, then the radiation detection system will be triggered to move the detectors. The predetermined time interval may be in the region of expected lifetime of the detector. Alternatively, the predetermined time interval may shorter, such that the detectors can be moved more often, such that they all receive a similar amount of radiation. This has the advantage that all the detectors break at a similar time and can then be replaced together.

The command to move the plurality of detectors can also be triggered when a detector in the imaging position has received a predetermined amount of radiation. This can be measured by monitoring the amount of radiation emitted by the source and calculating the expected amount of radiation received at the imaging location. Alternatively, another way to monitor the amount of radiation received by each detector is by using a radiation measurement device. The radiation measurement device is located on the side of the detector facing the source. The radiation measurement device is monitors the dose of radiation received by each detector. By way of example the radiation measurement device could be a Geiger Muller detector or a dose rate meter.

The radiation detection system produces an image, for example of a patient during radiotherapy treatment. Another way to trigger the command to move the plurality of detectors is when there is a deterioration in the image quality. This can be monitored by a computer system to determine the quality of the image and trigger when the quality falls below a predetermined threshold. Image quality metrics may include sharpness, blurriness, brightness, observing dead pixels and contrast monitoring.

The command may be triggered manually by an operator. The operator may be working in the field of radiotherapy treatment and when they identify that the detector is broken, they can send a command to trigger the radiation detection system to move the detectors.

After a detector 32b has deteriorated beyond use, the plurality of detectors are moved (e.g. the carousel 38 is rotated again) to position the next detector in the imaging position. This process can be repeated until all the detectors 36 have been used for imaging. After this time, all the detectors will have been exposed to the X-rays and therefore will be damaged, and the plurality of detectors (or carousel) is removed from the radiation detection system.

The plurality of detectors can also be moved such that each detector is used multiple times. This is done to even out the dose received by each of the detectors. In this way the detectors will break at the same time and therefore can all be replaced at the same time. Each detector will require calibration when moved into the imaging position, because in practice each detector is configured slightly different mechanically. Calibration of the detectors can be automatic.

The plurality of detectors may comprise a series of detectors, for example detectors that are capable of imaging different types of radiation or different sized lenses to allow the detector to image different locations at varying depths. Different lenses have different resolutions, these may be helpful to image different types of tissue.

In one embodiment, the detectors 36 are removed from the carousel 38, a new set of detectors 36 are housed in the carousel 38 and the carousel is re-inserted into the radiation detection system. Alternatively, a new carousel housing new detectors is inserted into the radiation detection system.

For replacement the entire carousel can be ejected from the radiotherapy device or moved to a replacement position, in which the carousel can be accessed by a technician and each detector can be replaced in turn.

The servicing of the detectors reduces the downtime of the radiation detection system when a detector is broken as a replacement detector can be used whilst the damaged detector (or set of detectors) awaits repair. Time spent repairing machines on site is costly and therefore it is desirable to replace as many detectors as possible when servicing. This reduces the number of callouts and time spent repairing the radiation detection system.

The radiotherapy device may also include a servicing position (not shown). A single detector or multiple detectors can be in the servicing position. The servicing position does not include the detector in the imaging position. For example, the servicing position may be located directly opposite the imaging position on the carousel 38 in FIG. 4. The servicing position may have a door (alternatively a cover or slide) that can be opened and closed. The door will be closed during operation of the radiation detection system to prevent any damage to the detectors. The door will open during servicing to allow detectors to be removed, replaced or repaired.

Detectors and cameras are increasingly low in cost and are easily replaceable. No reflector is needed in the radiation detection system of FIGS. 3, 4a and 4b, and the detector can be positioned directly beneath the source such that the radiation detection system can be considerably more compact. Reflectors must be precisely fitted and therefore increase the cost and complexity of manufacturing. Further, reflectors can have a limited lifespan, and once included in a radiation detection system can be difficult to replace. Therefore, removing the need for a reflector provides several advantages.

Additionally, the plurality of detectors (carousel) and/or the detector can be replaceable, resulting in an increased lifespan of the radiation detection system. The plurality of detectors being formed in a carousel provides a convenient and quick mechanism to move detectors into the imaging area.

Another advantage of the arrangement is that by using a plurality of detectors it is possible to use cheaper cameras.

Typically, expensive radiation resistant detectors are used in a radiation environment, however, by alternating the detectors and having a supply of working detectors that haven't been damaged it is possible to use non-radiation resistant detectors. These non-radiation resistant detectors are typically cheaper and produce a better image quality. The carousel allows these cheaper detectors to be used in turn when each one breaks.

The carousel can also take the form of a rotatable wheel comprising a plurality of detectors. The carousel can rotate in a vertical or horizontal direction to move the detectors into and out of the imaging position.

Belt or Chain

Figure 5:
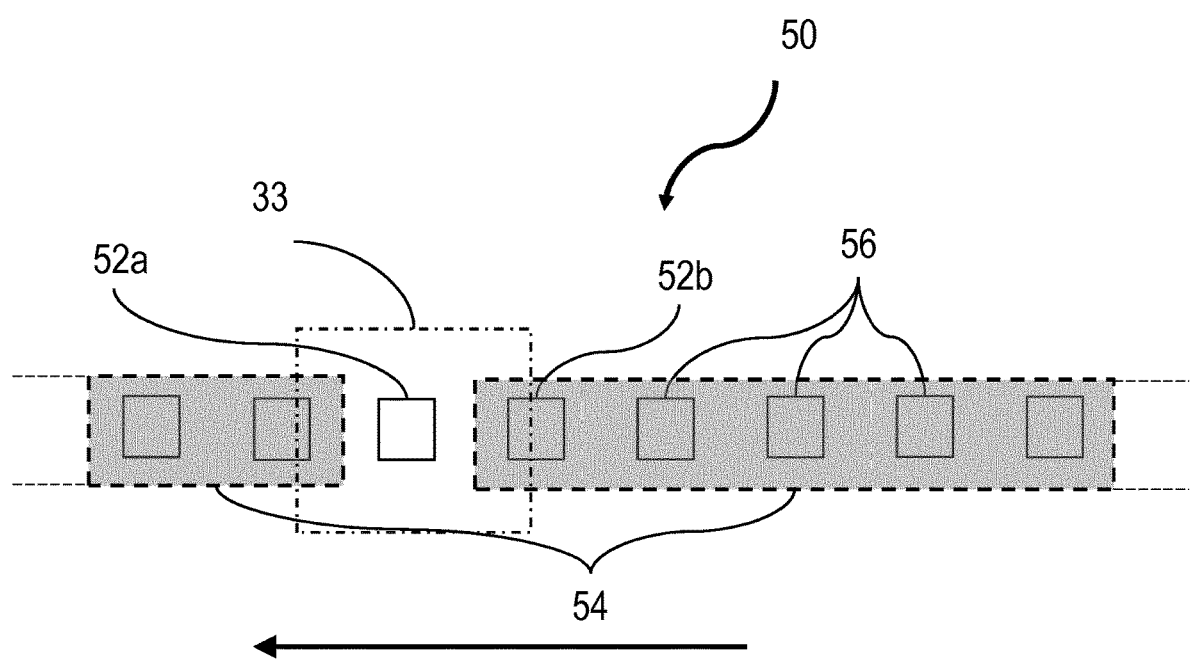
FIG. 5 illustrates a belt or chain system used in the radiation detection system of FIG. 3.

As shown in FIG. 5, the plurality of detectors can take the form of a belt 50 comprising a plurality of detectors 56, or a magazine comprising a plurality of detectors 56. The plurality of detectors 56 are positioned on a moveable belt or chain 50.

Detector 52a is positioned below a source 31 to directly image light or radiation (e.g. X-rays) 18 emitted from the source 31. The field of view of the light or radiation 18 detected and imaged by the detector 32a is shown by dotted lines 102 (see FIG. 3a). The detector 52a is positioned in an imaging position in the light or radiation path 18.

The belt 50 houses the plurality of detectors 56. The belt may be movable or slidable. The belt may move horizontally or vertically. Detector 52a is positioned in the imaging position. The imaging position is in the light or radiation path 18. In this position the detector 56a can image light or radiation emitted from the source 31. The remaining detectors 56 that are not in the imaging position are positioned outside of the light or radiation path 18. The detector in imaging position will experience damage from radiation (for example X-rays), and the detectors outside the radiation path are not exposed to the direct radiation. The detectors outside the radiation path are exposed to scattered radiation. The cross section of the path of the direct radiation is shown in FIG. 5 as the dashed line 33. As the remaining detectors are not in the path of radiation they will not receive direct radiation and therefore will experience less damage.

A radiation shield 54 can be placed above the detectors not in the imaging position 32a to help shield them from scattered radiation. The radiation shield 54 is configured to block the source from reaching detectors which are not in the imaging position. The radiation shield 34 may be used in addition to moving the detectors (other than the detector in the imaging position) out of the line of the cross section of the direct radiation path 33 to shield them from scattered radiation. Alternatively, all the detectors may be in the path of the radiation, however the shield can be used to block the radiation from reaching the detector which are not in the imaging position.

The shield 54 may have a hole overlaying the imaging position, wherein the hole is configured to allow the radiation or light 18 to reach the detector in the imaging position to directly image the source. The hole is located directly over the imaging position. The hole may extend to the edge of the shield, as shown in FIG. 5. Alternatively, the hole may be in the centre of the shield such that the hole does not extend to the edge of the shield (not shown).

The detector 52a images the source 31 from which light or radiation is emitted. The detector 52a will deteriorate through exposure to the radiation (for example X-rays) as it is sitting in the direct path of the radiation. When the detector has deteriorated beyond use or to a low quality, the plurality of detectors can move the detector 52a out of the imaging position and move the adjacent detector 52b into the imaging position. The belt or chain 50 will be moved along a position in the direction of the arrow as shown in FIG. 5. Detector 52b will not have previously been positioned in the cross section of the direct radiation path 33 (or will have been previously located behind a shield) and therefore will not have experienced the deterioration of detector 52a and will be useable to image light or radiation emitted from the source 31. Detector 52b can then be used to image the source 31 until it too deteriorates due to exposure to the radiation. This may take happen over the course of a number of different patient treatments.

The movement of the belt or chain 50 can be triggered by a command received by the radiation detection system. As previously discussed, this command can be triggered several different ways. For example, the movement may be triggered by a predetermined time interval, by receiving a predetermined amount of radiation, by a deterioration in the image quality or voluntarily by input from a person.

After a detector 52b has deteriorated beyond use, the belt is moved along a place again to position the next detector in the imaging position. This process can be repeated until all the detectors 56 have been used for imaging. After this time, all the detectors will have been exposed to the X-rays and therefore will be damaged, and the belt or chain is removed from the radiation detection system. In one embodiment, the belt 50 is removed, a new set of detectors 56 are housed in the belt 50 and the belt 50 is re-inserted into the radiation detection system. Alternatively, a new belt housing new detectors is inserted into the radiation detection system.

The belt or chain 50 may be a continuous loop. The belt or chain can have a servicing position to allow single or multiple detectors to be removed at once.

Bank

Figure 6A:
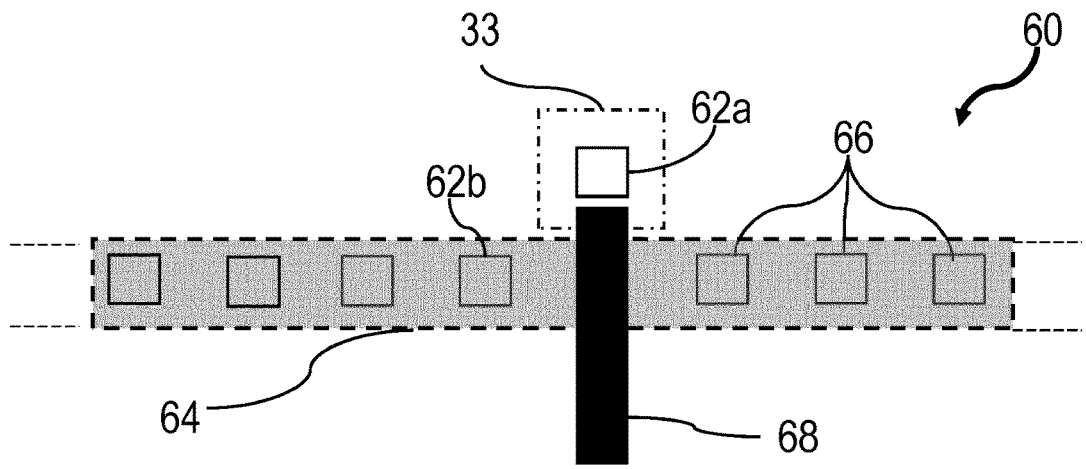
FIG. 6a-c illustrates a radiation detection system a bank system used in the radiation detection system of FIG. 3.
Figure 6B:
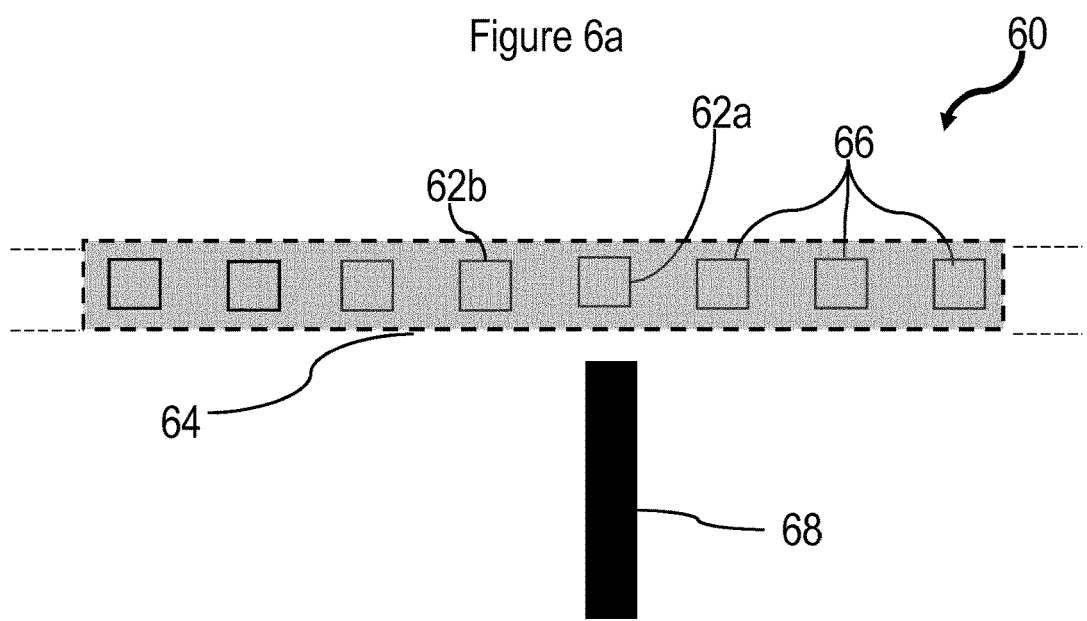
Figure 6C:
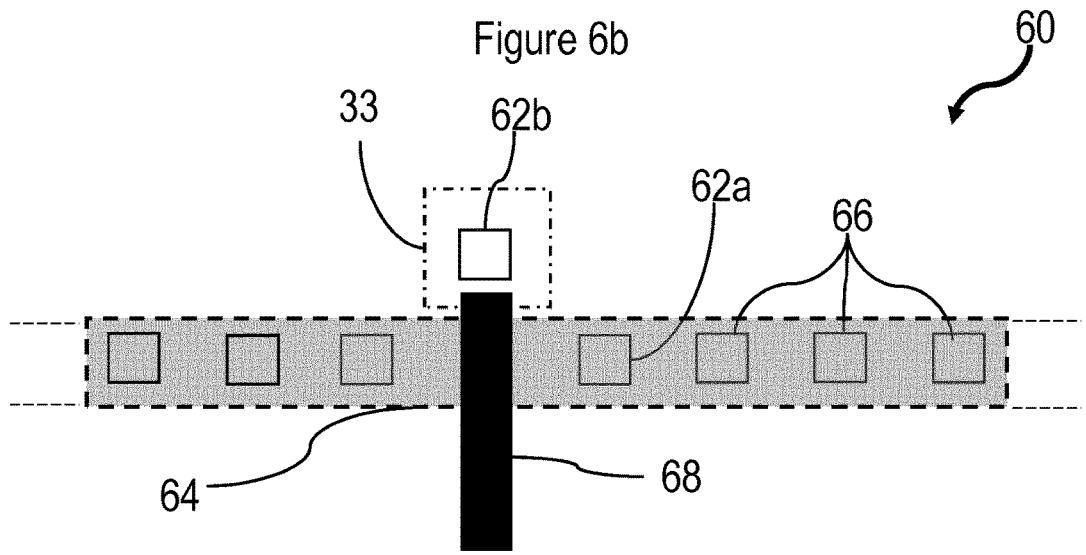

As shown in FIGS. 6a-6c, the plurality of detectors 66 can take the form of a bank 60 holding the plurality of detectors 66. The plurality of detectors 66 are positioned in a collection. In turn a detector may be selected for imagining. The plurality of detectors may be positioned in a line, as shown in FIGS. 6a-6c, however, other arrangements may be envisaged (e.g. a circular shape).

In FIG. 6a, detector 62a is positioned below a source 31 to directly image light or radiation (e.g. X-rays) 18 emitted from the source 31. The field of view of the light or radiation 18 detected and imaged by the detector 62a is shown by dotted lines 102 (see FIG. 3a). The detector 62a is positioned in an imaging position in the light or radiation path 18.

The bank 60 houses the plurality of detectors 66. The bank 60 may be stationary or moveable. The bank 60 comprises an actuation mechanism to move the plurality of detectors in turn into the imaging position. The actuation mechanism is configured to position one of the detectors into the imaging position in turn. The actuation means is may comprise an arm, for example the arm may be extendable, rotatable or otherwise moveable. The arm is discussed by way of example as an extendable arm 68.

The bank has an extendable arm 68. The extendable arm 68 is configured to push the respective detectors forwards into the imaging position and retract backwards to allow the detector to return into the bank. In FIG. 6a, the detector 62a is positioned in the imaging position. The imaging position is in the light or radiation path 18. In this position the detector 62a can image light or radiation emitted from the source 31. The remaining detectors 66 that are not in the imaging position are positioned outside of the light or radiation path 18. The detector in imaging position will experience damage from radiation (for example X-rays), and the detectors outside the radiation path are not exposed to the damaging radiation. The cross section of the path of the direct radiation is shown in FIG. 6a-c as the dashed line 33. As the remaining detectors are not in the direct path of radiation they will not receive radiation and therefore damage is minimised.

In some embodiments each detector may have its own respective extendable arm.

A radiation shield 64 can be placed above the detectors not in the imaging position 62a (FIG. 6a) to help shield them from scattered radiation. The radiation shield 64 is configured to block the source from reaching detectors which are not in the imaging position. The radiation shield 64 may be used in addition to moving the detectors (other than the detector in the imaging position) out of the line of the cross section of the direct radiation path 33 to shield them from scattered radiation. Alternatively, all the detectors may be in the path of the radiation, however the shield can be used to block the radiation from reaching the detector which are not in the imaging position (not shown).

The detector 62a images the source 31 from which light or radiation is emitted. The detector 62a will deteriorate through exposure to the radiation (for example X-rays) as it is sitting in the direct path of the radiation. When the detector has deteriorated beyond use or to a low quality, the bank and extendable arm can move the detector 62a out of the imaging position and another detector in the bank into the imaging position. The extendable arm 68 has at least one extended positions (shown in FIGS. 6a and 6b) and a retracted position (shown in FIG. 6b). The extendable arm 68 may extend to place a first detector 62a into the imaging position, see FIG. 6a. The extendable arm 68 may move horizontally, vertically or diagonally as required. Once the first detector has deteriorated beyond use, the extendable arm 68 will move into the retracted position and the first detector 62a will be moved to the bank 60. The first detector 62a will then be held with the plurality of detectors 66 (see FIG. 6b). Subsequently, a second detector 62b will be moved into the imaging position. The extendable arm 68 will move from the retracted position, into another extended position, pushing a second detector 62b into the imaging position (see FIG. 6c). Detector 62b will not have previously been positioned in the cross section of the direct radiation path 33 (or will have been previously located behind a shield) and therefore will not have experienced the deterioration of detector 62a and will be useable to image light or radiation emitted from the source 31. Detector 62b can then be used to image the source 31 until it too deteriorates due to exposure to the radiation. This may take happen over the course of several different patient treatments.

The movement of the extendable arm 68 can be triggered by a command received by the radiation detection system. As previously discussed, this command can be triggered several different ways. For example, the movement may be triggered by a predetermined time interval, by receiving a predetermined amount of radiation, by a deterioration in the image quality or voluntarily by input from a person.

After a detector 62b has deteriorated beyond use, the extendable arm again retracts and returns to the retracted position, then extends again moving another detector into the imaging position. This process can be repeated until all the detectors 66 have been used for imaging.

The extendable arm 68 extends to place each detector into the same imaging position when in the extended position. Alternatively, the extendable arm 68 may position each detector in a different position, the radiation detection system can be configured to account for the change in position of each detector.

The detectors can be moved into the imaging position in any order—they needn't be moved sequentially from left to right in FIG. 6. Being moved "in turn" does not necessarily refer to directly neighboring detectors but refers to any order of detectors being moved one by one into an imaging position.

The imaging position is not necessarily a singular point in space. Rather it is a location in which a detector can image radiation. The detector is exposed to more radiation when it is positioned in the imaging position than when it is not positioned in the imaging position. For example, in the embodiment of FIG. 6, each detector is in the imaging position when the arm is in the extended position, however the imaging position is not the same location for each detector. In contrast, in the carousal of FIG. 4, the imaging position is the same location for each detector.

After all the detectors will have been exposed to the X-rays and therefore are damaged, the bank of detectors can be removed from the radiation detection system. In one embodiment, the bank 50 is removed, a new set of detectors 56 are housed in the belt 50 and the belt 50 is re-inserted into the radiation detection system. Alternatively, a new belt housing new detectors is inserted into the radiation detection system.

The invention has been discussed with regards to a carousel, a belt or magazine and a bank with extendable arm. However, other arrangements may be envisaged. Any means for moving detectors into an imaging position one by one to directly image a source can be used.

The detectors throughout this disclosure image radiation from a source. The radiation may be: a source of treatment radiation, light reflected from a component of the radiotherapy device or from a patient in the radiotherapy device, light fluoresced from a source; light scintillated from a scintillator; or any other radiation.

Source of Radiation

The radiation detection system discussed in relation to the plurality of detectors, carousel, belt or bank of detectors may be configured to directly image radiation. The detector 32a is positioned below a source 31 to directly image radiation 18, in particular x-rays or gamma rays, emitted from the source 31. The field of view of the light or radiation 18 detected and imaged by the detector 32a is shown by dotted lines 102. The detector 32a is positioned in an imaging position in the radiation path 18.

The source of radiation could be an imaging source or a treatment source. Imaging a treatment source of information is used to determine the shape of the treatment beam. The treatment beam is shaped by a collimator, for example a multi-leaf collimator, according to a treatment plan. Imaging the treatment beam directly can be used to verify that the shape of the beam corresponds to the beam shape in the radiation plan.

Scintillator

Figure 7:
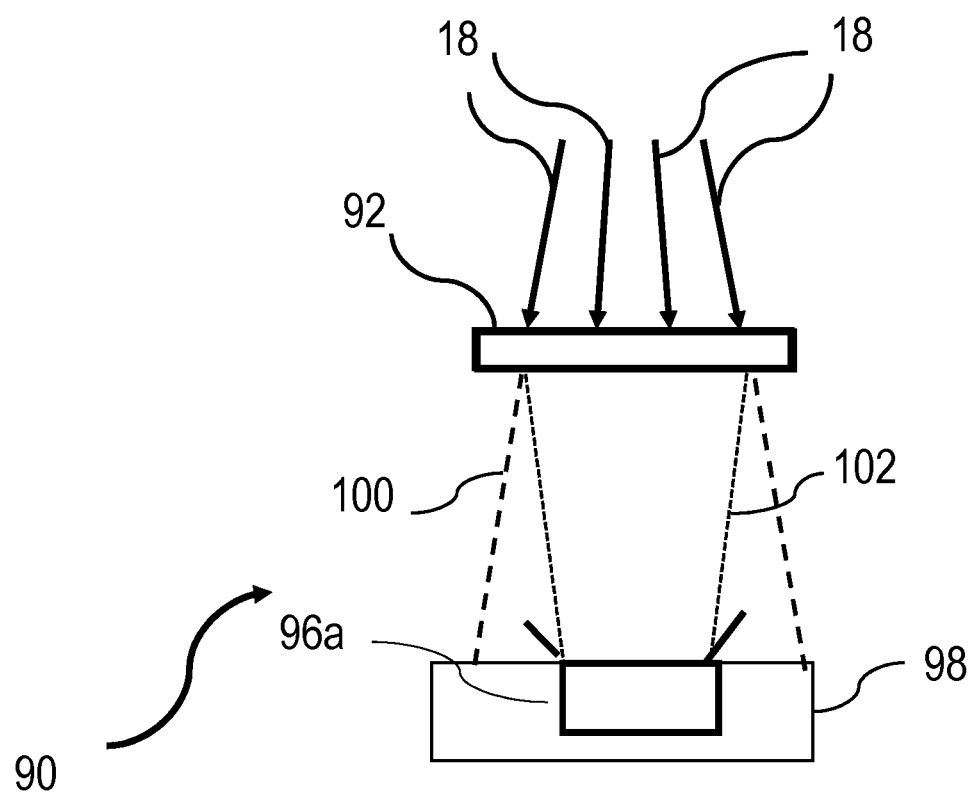
FIG. 7 illustrates a radiation detection system according to a second aspect of the present disclosure.

The radiation detection system discussed in relation to the plurality of detectors, carousel, belt or bank of detectors may be configured to image light from a scintillator for use in an X-ray radiation detection system which can image the intensity of radiation, for example once it has passed through a patient. FIG. 7 shows a radiation detection system having a scintillator 92, a plurality of detectors including detector 96a and a carousel 98 (the carousel may alternatively be a belt, chain or bank of detectors).

The scintillator 92 converts a portion of X-rays 18 to light. The scintillator converts photons of a first wavelength to photons of a second, longer wavelength. Detector 96a is positioned below the scintillator 92 to directly image light emitted from the scintillator. The field of view of the light detected and imaged by the detector is shown by dotted lines 102. Light which travels from the scintillator to the detector 96a creates an image of the scintillated light and by extension of the X-rays received by the scintillator. The path of the X-rays 18 which pass through the scintillator and are not converted to light is shown by dashed lines 100. The detector 96a is positioned in an imaging position in the X-ray path 100

In the imaging position the detector 96a can image light emitted from the scintillator 92. The remaining detectors (not shown) that are not in the imaging position are positioned outside of the direct X-ray path 100 or behind shielding. The detector in imaging position will experience damage from the X-rays, and the detectors outside the X-ray path are not exposed to the damaging X-ray radiation. A radiation shield (not shown) can be placed above the cameras not in the X-ray path 100 to help shield them from scattered radiation.

The remaining detectors (not shown) can be moved into the imaging position by using the apparatus described throughout the application. For example, the detectors may be rotated on a carousel. The detectors may be moved on a sliding belt or chain into the imaging position. The detectors may be moved into the imaging position using a bank of detectors and an extendable arm. These embodiments are described throughout this application and apply equally to light that may be imaged through a scintillator.

The camera 96a images the scintillator 92 from which light is emitted. The camera 96a will deteriorate through exposure to the X-rays passing through the scintillator. The movability of detectors allows detectors to be moved in and out of the x-ray radiation passing through the scintillator and allow a new detector to be used when a first detector has deteriorated beyond use. Shielding is used to block the plurality of detectors from exposure to scattered radiation. Shielding is placed everywhere other than where is strictly necessary to produce the desired image. There is a hole in the shielding to allow light from the scintillator to reach the detector.

The scintillator converts X-rays to light. However, in other aspects the scintillator can convert photons of a first wavelength of photos of a second, longer wavelength. Converting to light is beneficial, as mirrors and detectors (such as cameras) for optical photons are cheap and widely available. However, other wavelengths such as infrared (IR) or ultraviolet (UV) may also be suitable for such a purpose, and have the advantage that the container for the detector apparatus need not be so light tight, as stray optical light from the room will not affect IR or UV detectors, given appropriate filtering on the cameras.

Multi-Leaf Collimator

A 'multi-leaf collimator' (consists of a large number of elongate thin leaves arranged side to side in an array. Each leaf is moveable to be extended into the radiation field. The array of leaf tips can thus be positioned so as to define a variable edge to the collimator. Accurately knowing the position of each leaf is particularly important in the field of radiotherapy, where it is imperative to know the characteristics of the dose of radiation delivered to a patient.

A marker can be positioned on a leaf, or on each leaf of the multi-leaf collimator. A radiation detection system as described above can image light emitted, fluoresced or reflected from the marker. This can then be used to calculate the location of the leaf and therefore determine the collimator of the beam.

The radiation detection system may or may not be in located in the radiation beam, although scattered radiation will be present in the environment of the multi-leaf collimator in use. Therefore, it is beneficial to use the radiation detection system where only the detector in the imaging position is exposed to high levels of radiation. The radiation detection systems out of the imaging position do not experience the same level of deterioration as the detector in the imaging position.

Patient

The radiation detection system discussed in relation to the plurality of detectors, carousel, belt or bank of detectors may be configured to directly image a patient, for example to image their position during radiotherapy treatment. The detector is positioned to image light, this light can be produced from a source or may be reflected light or scattered by the radiotherapy device or patient. The detector is positioned in an imaging position in the path of light of the desired image.

Imaging of the patient is used to determine the location of the patient inside the radiotherapy device and is fed back into the treatment plan to ensure that treatment is delivered to the correct location inside the patient, for example to ensure radiation is directed towards tumours. This ensures that the minimum possible dose is used to treat patients and to prevent healthy cells and tissues from being damaged by the radiation treatment. The direct imaging of a patient is also used inside a CT scanner to monitor the location of the patient and accurately determine the location of imaging.

The radiation detection systems of any of the aspects illustrated in FIGS. 5 to 6, 7 and 8 can be used in a radiotherapy device. The radiation detection systems can be used in the position of the radiation detection system 20 illustrated in FIGS. 1a and 1b. There is also provided a radiotherapy device comprising a radiation detection system according to any of the above aspects. The radiotherapy device can treat or image a patient with radiotherapy from a source and the radiation detection system can image the patient using the radiation detection system as described above.

The above radiation detection systems may be imagers such as digital cameras, although other detectors could also be used. Digital cameras provide many advantages over other detectors including instant imaging, high quality of imaging and continuous imaging (i.e. video). Cameras in the above embodiments could be replaced with any conceivable detectors.

Method

There is also provided a method of operating a radiation detection system of any of the above embodiments.

The method of operating a radiation detection system comprising a plurality of detectors, the method comprises the steps of imaging a source of radiation using a first detector in an imaging position; receiving a command; upon receipt of the command, moving the first detector out of the imaging position and moving a second detector of the plurality of detectors into the imaging position.

The method may further comprise moving each of the plurality of detectors, in turn, to the imaging position. Each movement may be done on the receipt of a command. The detectors not in the imaging position are positioned out of the path of the radiation The command can be triggered several different ways. For example, the movement may be triggered by a predetermined time interval, by receiving a predetermined amount of radiation, by a deterioration in the image quality or voluntarily by input from a person.

The source of radiation could be any of: light from a scintillator; reflected light from a radiation source, a treatment source; light emitted or fluoresced from the leaf of a multi-leaf collimator.

The radiation detection systems could be positioned on a carousel and the moving of the first detector out of the imaging position and moving of a second detector of the plurality of detectors into the imaging position could comprise rotating the carousel.

The radiation detection systems could be positioned on a belt and the moving of the first detector out of the imaging position and moving of a second detector of the plurality of detectors into the imaging position could comprise moving or sliding the belt. The belt may move horizontally or vertically. The belt or chain will be moved along a position in the direction of the arrow as shown in FIG. 5, placing a new detector into the imaging position.

The radiation detection systems could be positioned in a bank and the moving of the first detector out of the imaging position and of moving a second detector of the plurality of detectors into the imaging position could comprise using an actuation mechanism such as an extendable arm. The extendable arm pushes the respective detectors forwards into the imaging position and retracts backwards to allow the detector to return into the bank. The bank and extendable arm can move a first detector out of the imaging position and another detector in the bank into the imaging position.

The methods described herein may be implemented by a computer program. The computer program may include computer executable code or instructions arranged to instruct a computer to perform the functions of one or more of the methods described above. The computer program and/or the code or instructions for performing such methods may be provided to an apparatus, such as a computer, on a computer readable medium or computer program product. The computer readable medium could be, for example, an electronic, magnetic, optical, electromagnetic, infrared, or semiconductor system, or a propagation medium for data transmission, for example for downloading the code over the Internet. Alternatively, the computer readable medium could take the form of a physical computer readable medium such as semiconductor or solid-state memory, magnetic tape, a removable computer diskette, a random-access memory (RAM), a read-only memory (ROM), a rigid magnetic disc, and an optical disk, such as a CD-ROM, CD-R/W or DVD.

Figure 8:
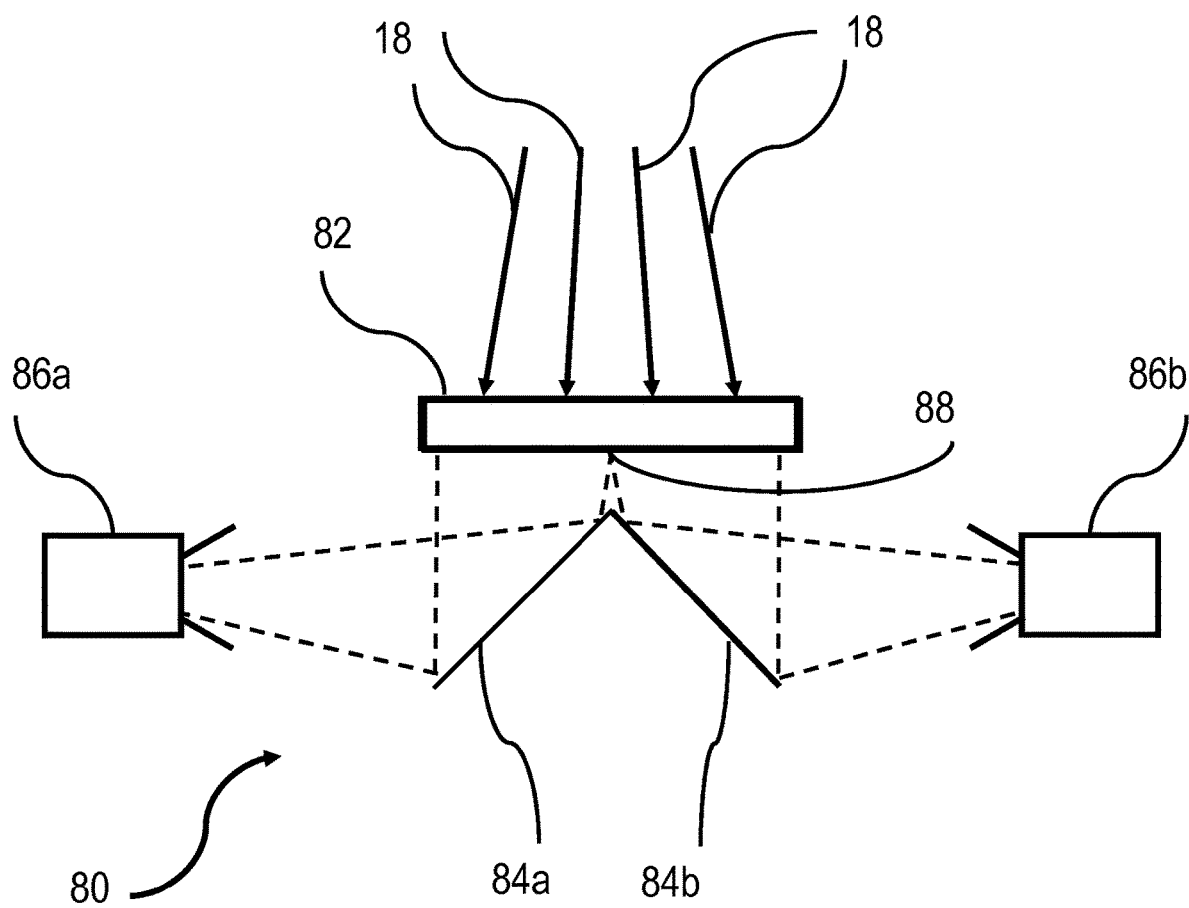
FIG. 8 illustrates an imager according to a first aspect of the present disclosure.
Figure 9A:
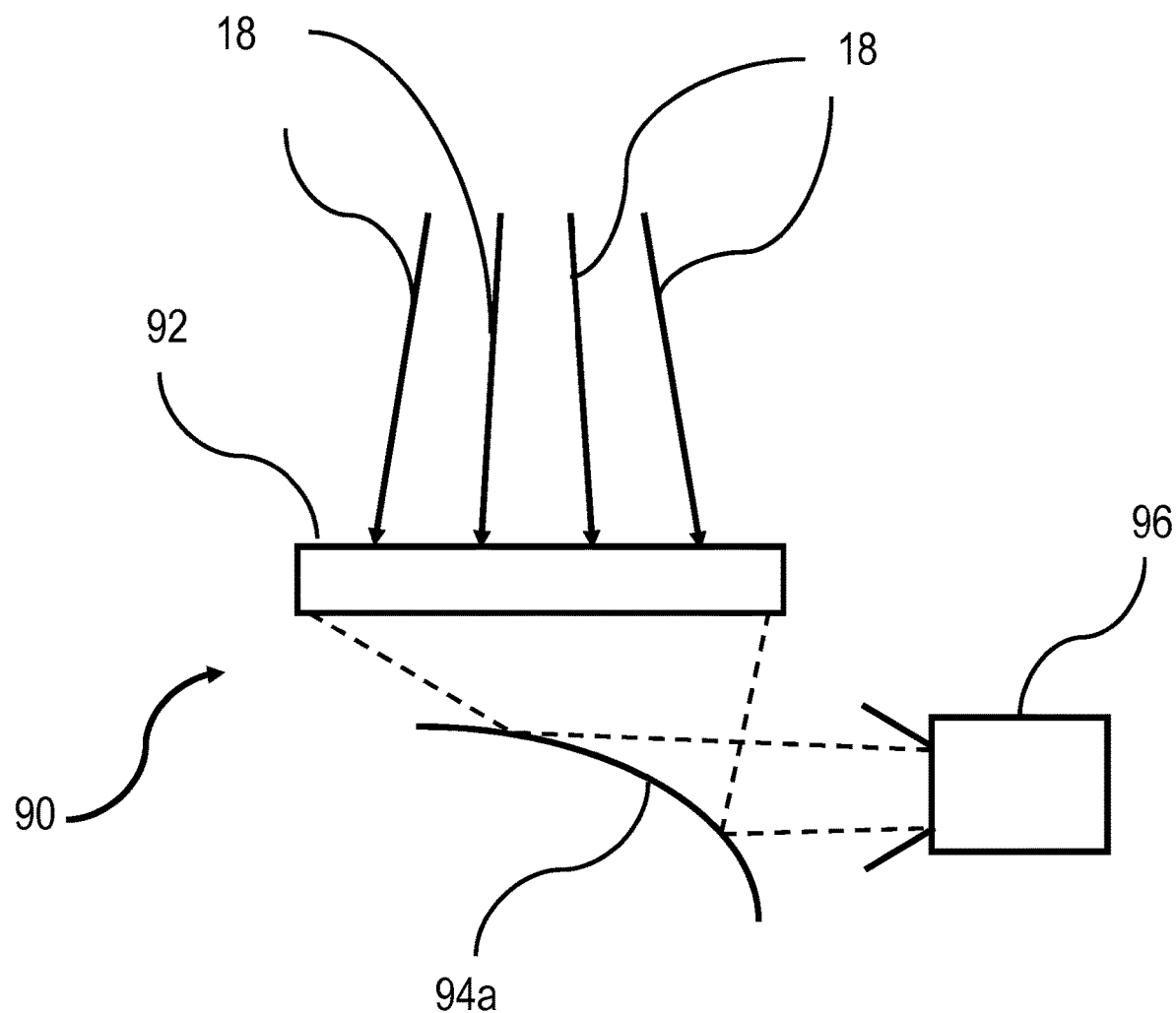
FIG. 9a illustrates an imager according to a second aspect of the present disclosure.
Figure 9B:
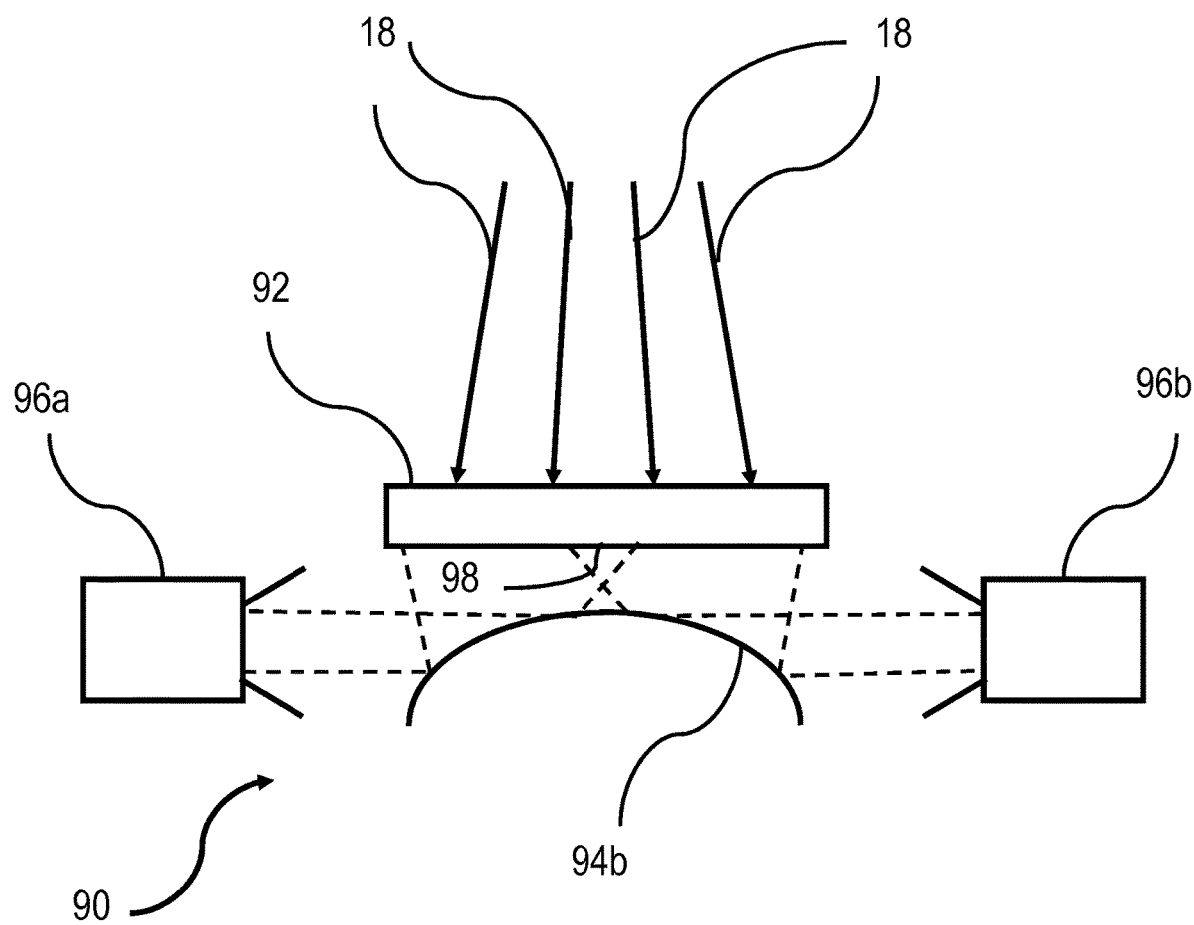
FIG. 9b illustrates an imager according to a third aspect of the present disclosure.
Figure 10:
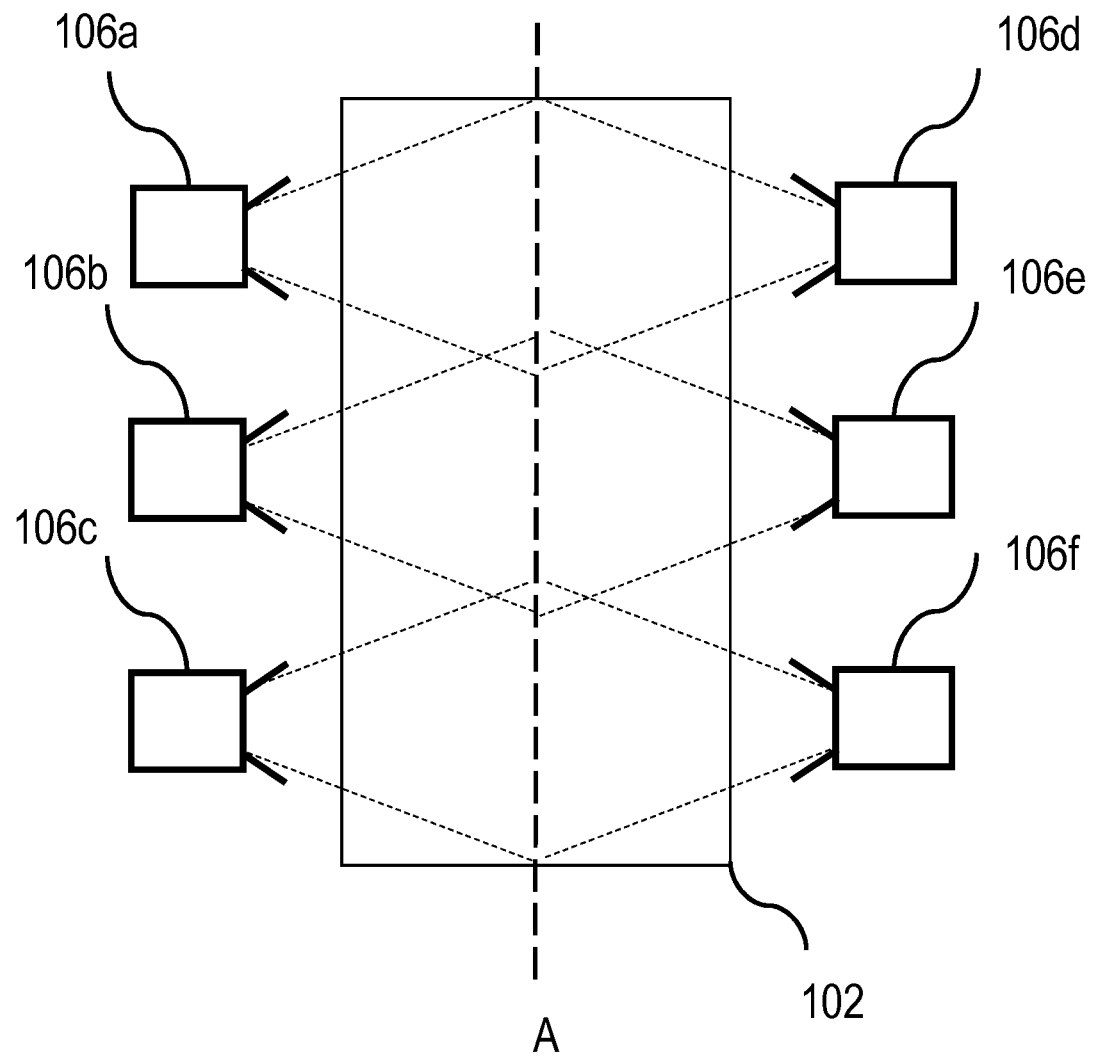
FIG. 10 illustrates a scintillator and a plurality of cameras from above.
Figure 11:
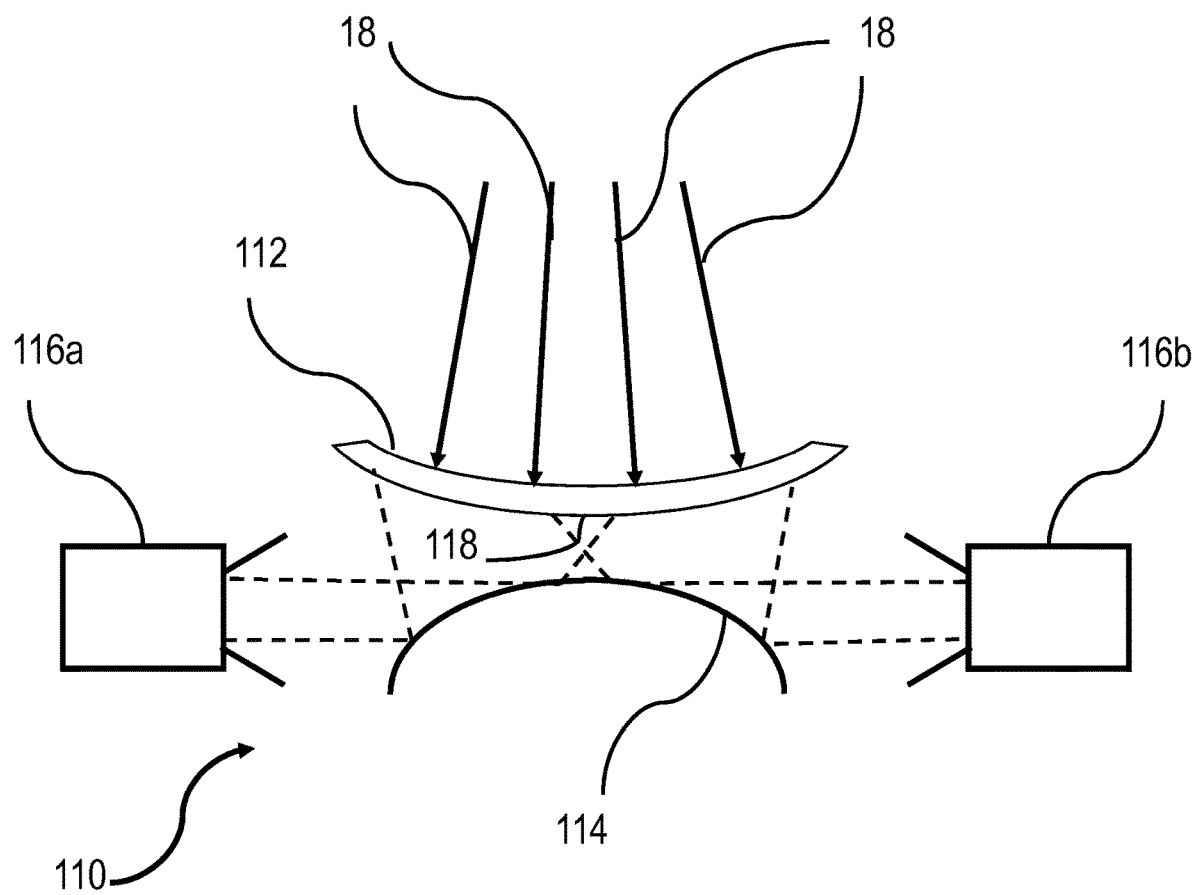
FIG. 11 illustrates an imager according to a fourth aspect of the present disclosure.
Figure 12:
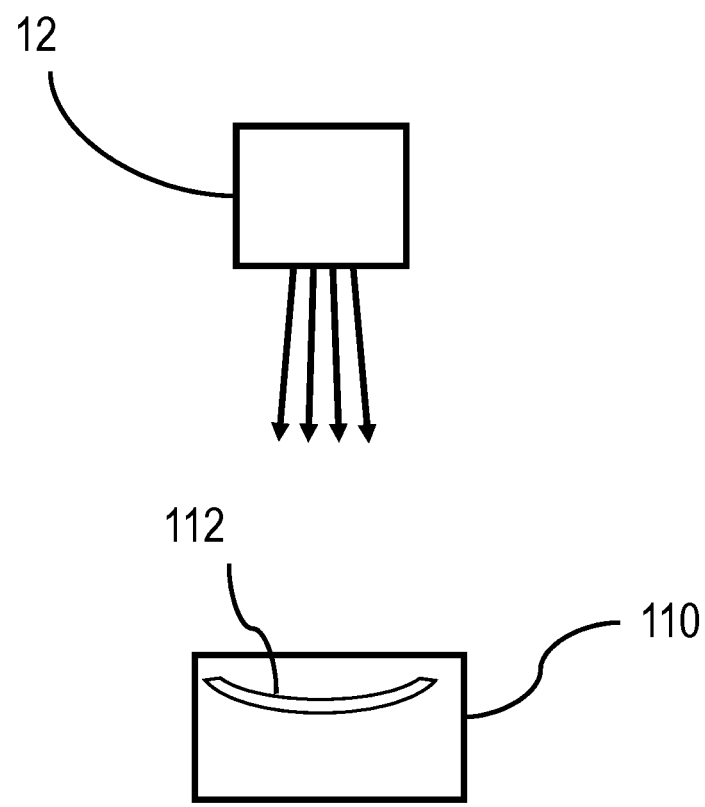
FIG. 12 illustrates the imager for FIG. 11 in a radiotherapy device.
Figure 13:
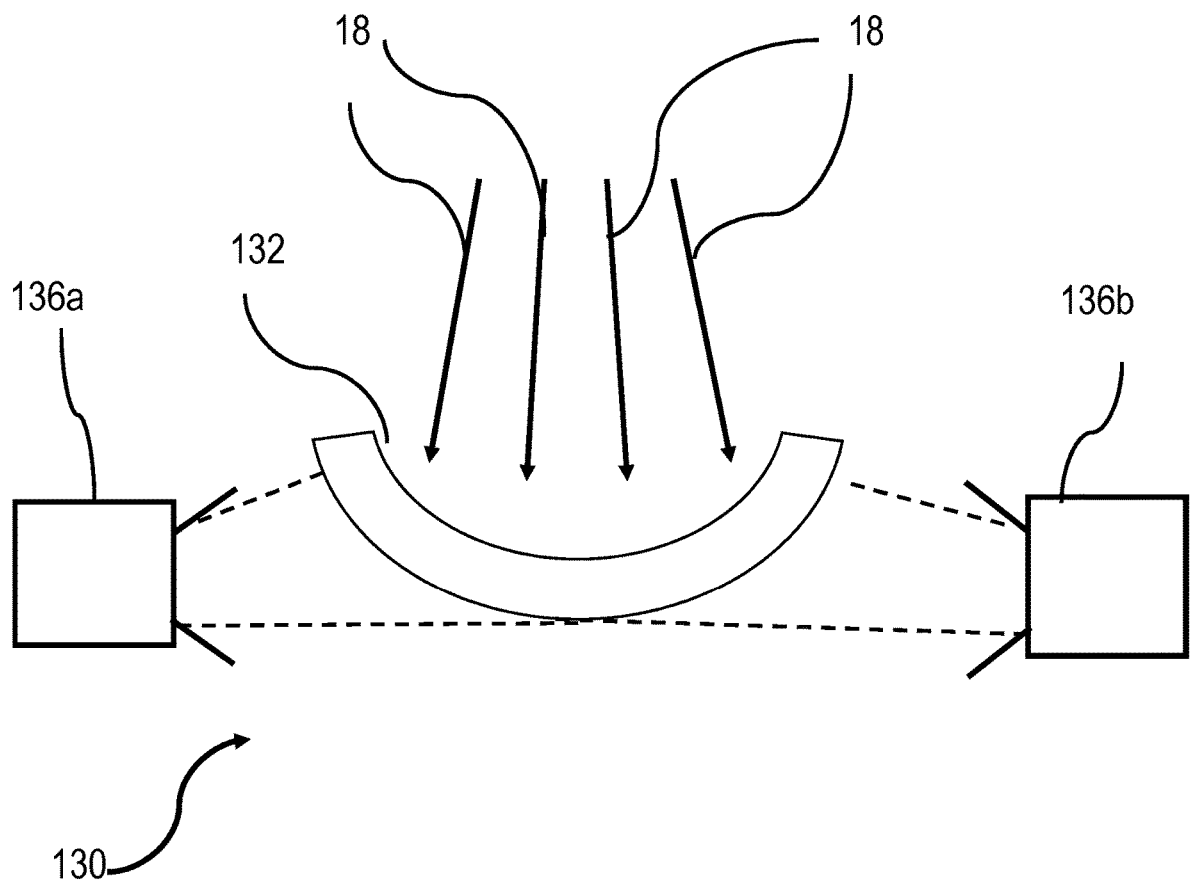
FIG. 13 illustrates an imager according to a fifth aspect of the present disclosure.
Figure 14A:
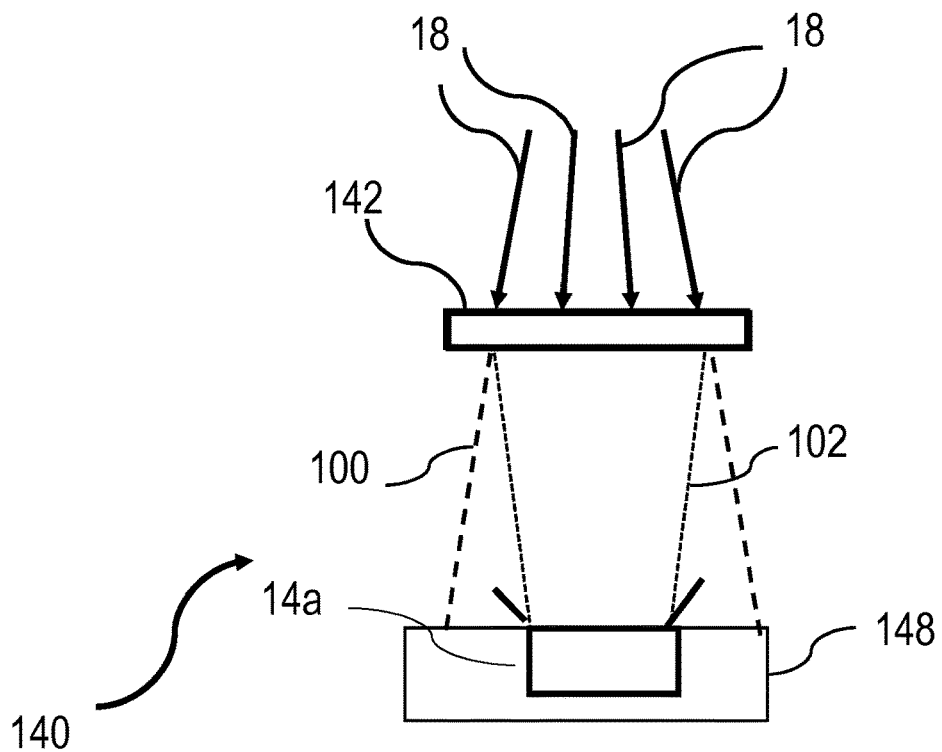
FIG. 14a illustrates an imager according to a sixth aspect of the present disclosure.
Figure 14B:
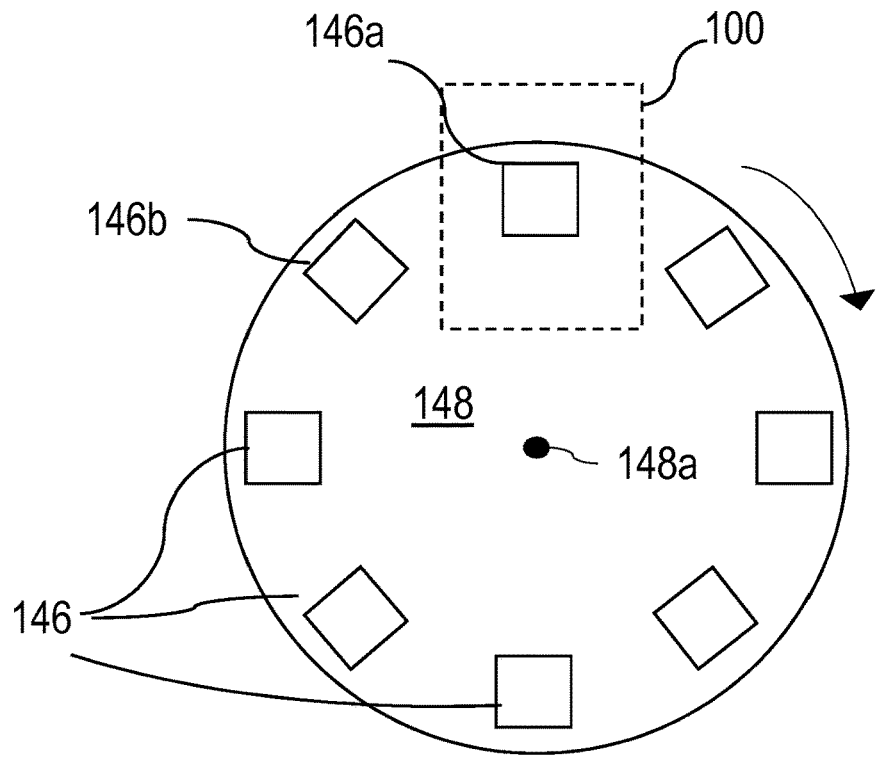

The following information is also disclosed herein:

FIG. 8 illustrates an imager according to a third aspect of the present disclosure;

FIG. 9a illustrates an imager according to a fourth aspect of the present disclosure;

FIG. 9b illustrates an imager according to a fifth aspect of the present disclosure;

FIG. 10 illustrates an imager according to a sixth aspect of the present disclosure;

FIG. 11 illustrates an imager according to a seventh aspect of the present disclosure;

FIG. 12 illustrates the imager of FIG. 11 in a radiotherapy device;

FIG. 13 illustrates an imager according to an eighth aspect of the present disclosure;

FIG. 14a illustrates an imager according to a ninth aspect of the present disclosure;

FIG. 14b illustrates a carousel used in the imager of FIG. 14a.

FIG. 8 shows an imager 80 in accordance with a first aspect of the present disclosure. The imager has a scintillator 82, two planar mirrors 84a and 84b and two cameras 86a and 86b. The planar mirrors are positioned facing away from one another, back-to-back, and angled at 45 degrees relative to the plane of the scintillator 82, and are positioned below the scintillator relative to the direction of impinging X-rays 18. The mirrors are aligned substantially with the middle of the scintillator. As in the imager in FIG. 2, the scintillator 82 converts a portion of X-rays 18 into light.

The first and second cameras 86a and 86b are focussed on the first and second mirrors 84a and 84b respectively. The first camera 86a is positioned to view a reflection in mirror 84a of a first portion of the scintillator. As the scintillator emits light in all directions, it will be understood that not all of the light emitted from the first portion of the scintillator will be reflected by the first mirror, only the light emitted from the first portion of the scintillator and in the direction of the first mirror will be reflected by the first mirror. The same understanding applies to reflectors throughout the disclosure.

The first camera 86a detects light reflected from the first mirror 84a and creates an image of the scintillated light from the first portion and by extension of the X-rays received at the first portion of the scintillator 82. The camera is a digital camera and sends the image as image data to a processor (not shown). The second camera 86b is positioned to view a reflection in mirror 84b of a second portion of the scintillator. The second camera detects the light reflected from the second mirror 84b and creates an image of the scintillated light from the second portion and by extension of the X-rays, received at the second portion of the scintillator 82. The camera is a digital camera and sends the image as image data to the processor (not shown). The images of the first portion from the first camera 86a and of the second portion from the second camera 86b are stitched together by the processor to create an image of the scintillated light as viewed by the two cameras.

The first and second portions are different, but there is a region 88 where the first and second portions overlap. This is useful when processing the image data from the cameras 86a and 86b. Partial overlap of the imaged sections allows for accurate reconstruction of the complete imaging area when stitching the images together. That is, images from the different cameras can be aligned correctly using the common imaged area.

The imaging area of the scintillator is divided into different fields of view which are imaged by two cameras, via the two back-to-back planar mirrors, each being angled at 45° to the scintillator. Because each camera now only has to image half of the scintillator, the depth of the mirror portion of the imager 80 is half the width of the total imaging area. Therefore, the depth of the imager is reduced by around 50% compared to the prior art imager illustrated in FIG. 2. The depth might not be reduced by exactly 50%, as the depth of the scintillator, although small, contributes to the depth of the imager, and there may be a gap between the mirror(s) and the scintillator.

FIG. 9a shows an imager 90 in accordance with a second aspect of the present disclosure. The imager 90 comprises a scintillator 92, a curved mirror 99a and a camera 96. As with the imager in FIG. 8, the scintillator converts a portion of X-rays 18 into light. Light emitted from the scintillator 92 is reflected from the curved mirror 99a towards the camera 96. The curvature of the mirror results in infinitesimal reflective portions angled respective to one another. The tangents of different portions of the curved mirror are at different angles relative to the light received from the scintillator, and therefore the different portions reflect the light in different directions. The light is reflected towards the camera 96. The camera creates an image of the scintillated light and by extension of the X-rays received by the scintillator. The entire imaging area is imaged by the camera, but the image is distorted due to the curvature of the mirror. The camera sends the image to a processor (not shown). The distortion caused by the curved mirror and recorded by the camera can be corrected via known calibration and processing techniques.

The depth of the curved mirror is less than the width of the scintillator. The curvature of the mirror 99 allows the camera to image a greater area of the scintillator (i.e. it increases the divergence of the camera's view). The curvature of the mirror therefore reduces the depth of the imager compared to the prior art.

FIG. 9*b* shows an imager 90 in accordance with a third aspect of the present disclosure. The imager 90 comprises a scintillator 92, a curved mirror 99*b* and two cameras 96*a* and 96*b*. As in the above imagers, the scintillator 92 converts a portion of the X-rays 18 into visible light.

The first and second cameras 96*a* and 96*b* are focussed on first and second sides of the curved mirror 99*b*, so that in the reflection of the mirror, they can image the first and second portions of the scintillator. The first camera 96*a* images a first portion of the scintillator via a reflection in the first side of the curved mirror 99*b*. The first camera detects the light and creates an image of the of the scintillated light from the first portion and by extension of the X-rays received at the first portion of the scintillator. The camera sends the image to a processor (not shown). The second camera 96*b* images a second portion of the scintillator via a reflection in the second side of the curved mirror 99*b*. The second camera detects the light and creates an image of the scintillated light from the second portion and by extension of the X-rays received at the second portion of the scintillator. The camera sends the image to the processor.

The images created by the first and second cameras will be distorted due to the curvature of the mirror. The distortion includes geometrical distortion and intensity distortion. The intensity distortion translates to a dose distortion, as the intensity of the light is proportional to the amount of radiation. The distortion caused by the curved mirror can be corrected via known calibration and processing techniques.

The images of the first portion from the first camera 96*a* and of the second portion from the second camera 96*b* are stitched together by the processor to create an image of the scintillator. The images can be stitched together after the correction of the distortion in the images, or before the correction of the distortion in the images.

There is a region 98 where the imaging areas of the first and second cameras 96*a* and 96*b* overlap. This is useful when processing the image data from the cameras, as the overlap allows for accurate reconstruction of the complete imaging area when stitching the images together. That is, images from the different cameras can be aligned correctly using the common imaged area.

The cameras 96*a* and 96*b* are positioned either side of the scintillator 92 and mirror 99*b*. This alters the layout of the apparatus compared to an imager with a single detector.

As in the imager FIG. 8, in the imager 40 the imaging area of the scintillator is divided into different fields of view which are imaged by different cameras. As in the imager of FIG. 4*a*, the depth of the curved mirror 44*b* is less than the width of scintillator. The curvature of the mirror causes the imaging area of each camera to be expanded (i.e. it increases the angular range over which the camera can capture an image), and the depth of the mirror portion of the imager is less than the width of the scintillator. Therefore, the depth of the imager is reduced compared to the prior art.

The above aspects in FIGS. 8, 9*a* and 9*b* reduce the depth of the imager by providing a mirror with non-planar portions, which increases the respective fields of view of the cameras. The depth of the mirror portion of the imager in each aspect is less than the width of the imaging area.

It will be appreciated that various alterations can be made to the above aspects. For example, features can be combined from each of the above aspects.

A combination of planar and curved mirrors could be used in any suitable arrangement. A single mirror with angled planes could replace the two separate mirrors in FIG. 2. Mirrors facing away from each other can be used. In an aspect, planar mirrors are angled at angles other than 45 degrees to the imaging area. In the above aspects, the cameras are all angled to detect light travelling parallel to the plane of the imaging area. However, cameras could be angled to detect light at other angles to the imaging area.

One advantageous arrangement may be to reduce the angle of the mirror relative to the horizontal, for example to 80°. The camera can then be angled such that top of the camera is in roughly the same plane as the top of the scintillator, being directed towards the mirror. The camera and mirror angle result in the camera imaging an area of the scintillator reflected from the mirror.

It will be appreciated that the imager is not limited to a certain angle of the mirrors relative to the horizontal. Any number of mirror angles and camera arrangements can be utilized.

Non-planar reflective portions include reflective portions which do not form a single plane. A reflector arrangement may also be referred to as a reflector.

In an aspect, instead of curved mirrors a plurality of planar portions approximating a curve are included in the imager.

The scintillators in any of the aspects could be curved or planar. In an aspect, a non-planar scintillator with a non-planar imaging area is used, for example a scintillator having planar portions angled relative to one another and approximating a curve is used.

In a further aspect an imager has n mirrors and n corresponding detectors, each detector positioned to image a respective portion of the imaging area via a mirror. The mirrors could be curved mirrors, or planar mirrors with the plane of the mirrors angled relative to the plane of at least one other mirror.

Such an example is shown in FIG. 10, which illustrates a scintillator 102 and a plurality of cameras 106*a*-106*f* from above. In use radiation will travel into the page. The scintillator has a major axis A. Below the scintillator is a reflector arrangement aligned along the major axis. The arrangement could be an extension of the arrangement shown in FIG. 8, 9*a* or 9*b*, with a series of non-planar mirrors and detectors aligned in a direction coming out of the page of these figures. As in FIGS. 8, 9*a* and 9*b*, cameras are positioned beneath the scintillator, spaced away from directly underneath the scintillator and therefore out of the path of the radiation. Each camera is angled towards the arrangement to view a reflection in the arrangement of a portion of the scintillator. The dashed lines show the field of view of each of the cameras. With the cameras spaced along the direction of the major axis of the scintillator, the area of imaging can be increased relative to the arrangements shown in FIGS. 8, 9*a* and 9*b* without requiring a large solid state imager or depth to accommodate a wide mirror. The imaging area can be divided up and standard cameras can be used. Therefore, a large imaging area can be imaged without requiring a large camera or a large mirror. This arrangement could be scaled up to any size of imaging area and could be used with a large curved scintillator.

In FIG. 10 cameras are positioned on both sides of the scintillator. However, it will be appreciated that in other arrangements, for example using the reflector arrangement of FIG. 9a, cameras could all be positioned only on one side of the scintillator.

FIG. 11 illustrates an imager 110 according to a fourth aspect of the present disclosure. The imager 110 comprises a curved scintillator 112, a curved mirror 114 and two cameras 1111a and 1111b. The scintillator 112 converts a portion of X-rays 18 to light as in the other imagers. The field of view of the first and second cameras 1111a and 1111b is reflected from the curved mirror 114 to image light emitted from first and second portions of the scintillator respectively. The first and second cameras create images of the scintillated light from the first and second portions respectively, which can be combined to create and image of the entire imaging area as in the imager in FIG. 10. As in the imager of FIG. 10, the images are distorted and are corrected using calibration techniques. There is overlap 118 of the first and second portions of the scintillator.

The imager 110 is shown in a radiotherapy device in FIG. 12, with like reference numerals being used to denote like features. The camera and mirrors of the imager 110 are not shown in FIG. 12. The radiotherapy device has a radiation source 12. The loci of the curvature of the scintillator 112 is positioned close to or on the source of radiation so that the distance between the source 12 and the scintillator 112 remains constant even over a wide-angle range. Because the intensity of the X-ray radiation drops off as $1/x^2$, the signal from a region of the scintillator further from the source will appear less intense than the signal from a region of the scintillator closer to the source. Changes in intensity reflect the density of the material the X-rays have passed through within the patient, or the distance between the radiation source and the imager, so it is important to understand where the variations in the signal intensity come from. By curving the scintillator around a focal point at the radiation source, all regions of the scintillator are at a common distance from the source, thus removing the $1/x^2$ intensity variation, making it easier to calibrate the images acquired from the scintillator, and therefore reducing the calibration required to obtain a clear image from the apparatus.

In FIGS. 11 and 12 the curvature of the scintillator runs across the page. However, the scintillator could instead be curved in the tangential plane (i.e. perpendicular to the plane of the image), or in both axes so as to subtend some portion of a curved cylinder.

As will be appreciated from the below description, a major advantage of providing a curved scintillator is to allow a larger area to be imaged without requiring the expense of a large solid-state imager, and is to the overall size of the mirror and camera arrangement is smaller compared to known imagers. Accordingly, a radiotherapy device using a curved scintillator can have a large imaging area whist maintaining a relatively small space around or behind the scintillator. This saves space in radiotherapy devices, where previously a large volume would be required to accommodate the imager of a large imaging area.

FIG. 13 shows an imager 130 in accordance with a fifth aspect of the present disclosure. The imager 130 comprises a curved scintillator 132 and two cameras 136a and 136b.

The scintillator 132 converts a portion of X-rays 18 to light as in the previous imagers, which is emitted in all directions. Cameras 136a and 136b are positioned to the side of the scintillator 132 such that the cameras are out of the path of the X-rays travelling through the scintillator. The cameras are directed at the scintillator to detect light from the scintillator. The curvature of the scintillator means that every portion of the underside of the scintillator can be viewed by at least one of the cameras. Camera 136a images a first portion of the imaging area and camera 136b images a second portion of the imaging area. The images from each of the cameras are stitched together to form a complete image of the imaging area. As with the previous aspects, there may be overlap in the portions.

The cameras 136a and 136b are positioned outside the path of the X-rays and therefore are not exposed to the damaging X-ray radiation. This increases the life span of the cameras and the imager. There is no mirror required, reducing the size of the imager. The imager is therefore easier and cheaper to manufacture.

FIG. 14a shows an imager according a sixth aspect of the present disclosure. The imager has a scintillator 142, a plurality of cameras including camera 146a and a carousel 148. The carousel 148 is shown from above in FIG. 14b.

The scintillator 142 converts a portion of X-rays 18 to light. Camera 146a is positioned below the scintillator 142 to directly image light emitted from the scintillator. The field of view of the light detected and imaged by the camera is shown by dotted lines 102. Light which travels from the scintillator to the camera 146a creates an image of the scintillated light and by extension of the X-rays received by the scintillator. The path of the X-rays 18 which pass through the scintillator and are not converted to light is shown by dashed lines 100. The camera 146a is positioned in an imaging position in the X-ray path 100.

The carousel 148 houses the plurality of cameras 146. The carousel is rotatable about an axis 148a. Camera 146a is positioned in the imaging position. The imaging position is in the X-ray path 100. In this position the camera 146a can image light emitted from the scintillator 142. The remaining cameras 146 that are not in the imaging position are positioned outside of the X-ray path 100. The camera in imaging position will experience damage from the X-rays, and the cameras outside the X-ray path are not exposed to the damaging X-ray radiation. A radiation shield (not shown) can be placed above the cameras not in the X-ray path 100 to help shield them from scattered radiation.

The camera 146a images the scintillator 142 from which light is emitted. The camera 146a will deteriorate through exposure to the X-rays passing through the scintillator. When the camera has deteriorated beyond use or to a low quality, the carousel 148 can be rotated about axis 148a as shown by the arrow in FIG. 14b and can move the camera 146a out of the imaging position and move the adjacent camera 146b into the imaging position. Camera 146b will not have previously been positioned in the X-ray path 100 and therefore will not have experienced the deterioration of camera 146a and will be useable to image light emitted from the scintillator 142. Camera 146b can then be used to image the scintillator 142 until it too deteriorates due to exposure to the X-rays. This may take happen over the course of a number of different patient treatments.

After camera 148b has deteriorated beyond use, the carousel is rotated again to position the next camera in the imaging position. This process can be repeated until all of the cameras 146 have been used for imaging. After this time, all of the cameras will have been exposed to the X-rays and therefore will be damaged, and the carousel is removed from the imager. The cameras 146 are removed from the carousel, a new set of cameras are housed in the carousel and the carousel is re-inserted into the imager. Alternatively, a new carousel housing new cameras is inserted into the imager.

Cameras are increasingly low in cost and are easily replaceable. No reflector is needed in the imager of FIGS. 14a and 14b, and the camera can be positioned directly beneath the scintillator such that the imager can be considerably more compact. Further, the carousel and/or the detector can be replaceable, resulting in an increased lifespan of the imager as a whole. The carousel provides a convenient and quick mechanism to move cameras into the imaging area.

A carousel can take the form of a belt comprising a plurality of camera, or a magazine comprising a plurality of cameras, or a rotatable wheel comprising a plurality of cameras. Other arrangements may be envisaged.

Any means for moving detectors into an imaging position one by one to directly image scintillated light from a scintillator can be used.

The imagers of any of the aspects illustrated in FIGS. 8 to 11, 13 and 14 can be used in a radiotherapy device. The imagers can be used in the position of the imager 20 illustrated in FIGS. 1a and 1b. There is also provided a radiotherapy device comprising an imager according to any of the above aspects. The radiotherapy device can treat or image a patient with radiotherapy from a source and the imager can image the patient using the imager as described above.

The above imagers use digital cameras, although other detectors could also be used. Digital cameras provide many advantages over other detectors including instant imaging, high quality of imaging and continuous imaging (i.e. video). The above aspects include mirrors, although any reflectors can be used. Cameras in the above embodiments could be replaced with any conceivable detectors.

The scintillators of the above imagers convert X-rays to light. However, in other aspects the scintillator can convert photons of a first wavelength of photons of a second, longer wavelength. Converting to light is beneficial, as mirrors and detectors (such as cameras) for optical photons are cheap and widely available. However, other wavelengths such as infrared (IR) or ultraviolet (UV) may also be suitable for such a purpose, and have the advantage that the container for the detector apparatus need not be so light tight, as stray optical light from the room will not affect IR or UV detectors, given appropriate filtering on the cameras.

Directly imaging the scintillator refers to imaging converted photos received at the camera without being reflected from a mirror.

Non-planar is used throughout to mean not in a flat plane. This could include a surface with two or more flat portions angled relative to one another, or a curved surface.

Thus there is provided an imager for a radiotherapy device, and a radiotherapy device comprising an imager.

Features of the above aspects can be combined in any suitable manner. It will be understood that the above description is of specific embodiments by way of aspect only and that many modifications and alterations will be within the skilled person's reach and are intended to be covered by the scope of the appandant clauses.

Disclosed herein are the following numbered clauses:

Clause 1. An imager comprising:
a scintillator configured to convert photons of a first wavelength to photons of a second, longer wavelength;
a reflector arrangement comprising non-planar reflective portions; and
at least one detector positioned to image at least a portion of the scintillator via the reflector.

Clause 2. An imager according to clause 1, wherein each non-planar portion is configured to reflect converted photons from the scintillator to a respective field of view.

Clause 3. An imager according to clause 1 or 2, wherein the reflector arrangement comprises a curved mirror, or wherein the non-planar portions are each planar and angled with respect to one another.

Clause 4. An imager according to any preceding clause, wherein the imager comprises a first detector and a second detector, and wherein:
a first reflective portion of the reflector arrangement is configured to reflect converted photons from a first section of the scintillator in a first direction to a first field of view, and a second reflective portion of the reflector arrangement is configured to reflect converted photons from a second section of the scintillator in a second, different direction to a second field of view;
the first detector is positioned to detect converted photons in the first field of view to image the first section of the scintillator; and
the second detector is positioned to detect converted photons in the second field of view to image the second section of the scintillator.

Clause 5. An imager according to clause 4, wherein the first and second sections are different.

Clause 6. An imager according to clause 5, wherein the first and second sections partially overlap.

Clause 7. An imager according to any of clauses 4 to 6, wherein the first reflective portion is a first planar mirror and the second reflective portion is a second planar mirror and wherein the first and second mirrors face away from one another.

Clause 8. An imager according to clause 7, wherein the scintillator is planar and wherein each mirror is angled at 45 degrees to a plane of the scintillator.

Clause 9. An imager according to any preceding clause, wherein the reflector arrangement comprises n mirrors and the imager comprises n detectors, each detector being configured to image a portion of the imaging area via a respective mirror.

Clause 10. An imager according to clause 1, 2 or 3 comprising a single detector.

Clause 11. An imager according to any preceding clause, wherein the scintillator is planar.

Clause 12. An imager according to any of clauses 1 to 10, wherein the scintillator is curved.

Clause 13. An imager comprising:
a curved scintillator configured to convert photons of a first wavelength to photons of a second, longer wavelength; and
at least one detector positioned to image at least a portion of the scintillator.

Clause 14. An imager according to clause 13, wherein the at least one detector is positioned to directly image the scintillator.

Clause 15. An imager according to clause 13, further comprising a reflector, wherein the at least one detector is positioned to image at least a portion of the scintillator via the reflector.

Clause 16. An imager comprising:
a scintillator configured to convert photons of a first wavelength to photons of a second, longer wavelength; and a plurality of detectors moveable to position each detector in turn in an imaging position to directly image the scintillator.

Clause 17. An imager according to any preceding clause, wherein the scintillator is configured to convert X-rays to photons of a longer wavelength.

Clause 18. An imager according to clause 17, wherein the scintillator is configured to convert X-rays to visible light.

Clause 19. A radiotherapy device comprising an imager according to any of clauses 1 to 18.

The invention claimed is:

1. A radiation detection system for a radiotherapy device comprising:
   a plurality of detectors moveable to position each detector in turn in an imaging position to detect radiation;
   wherein the radiation detection system is configured to, upon receipt of a command, move a first detector out the imaging position and move a into the imaging position, , wherein the command is triggered by at least one of:
   a specified time interval;
   first detector having received a specified amount of radiation; and
   wherein the radiotherapy device produces an image, and wherein the command is triggered by a deterioration in quality of the image.

2. The radiation detection system according to claim 1, wherein a carousel houses the plurality of detectors and the carousel is rotatable about an axis to position each detector in turn in the imaging position.

3. The radiation detection system according to claim 2, wherein when the carousel is rotated about the axis a first detector is moved out of the imaging position and a second detector is moved into the imaging position.

4. The radiation detection system according to claim 1, wherein the plurality of detectors are positioned on a moveable belt or chain.

5. The radiation detection system according to claim 4, wherein when the chain or belt is moved a first detector is moved out of the imaging position and a second detector is moved into the imaging position.

6. The radiation detection system according to claim 1, wherein the plurality of detectors are positioned in a bank, wherein the bank is configured to position one of the detectors into the imaging position in turn.

7. The radiation detection system according to claim 6, wherein the bank further comprises an actuation mechanism, wherein the actuation mechanism pushes forward one of the detectors into the imaging position in turn.

8. The radiation detection system according to claim 7, wherein the actuation mechanism is an extendable arm.

9. The radiation detection system according to claim 1, further comprising a shield configured to block a source from reaching detectors which are not in the imaging position.

10. The radiation detection system according to claim 9, wherein the shield defines a hole overlaying the imaging position, wherein the hole is configured to allow the source to reach the detector in the imaging position to image the source.

11. The radiation detection system according to claim 1, wherein each detector further comprises a radiation measurement device, configured to monitor a dose of radiation received by each detector.

12. The radiation detection system according to claim 1, wherein the radiation detection system is configured to allow the removal or replacement of the detectors.

13. The radiation detection system according to claim 1, further comprising a servicing position, wherein a detector is locatable in the servicing position and the servicing position is configured to allow the removal or replacement of the detector.

14. The radiation detection system of claim 1, in combination with an imager, the combination comprising:
   a scintillator configured to convert photons of a first wavelength to photons of a second, longer wavelength; and
   wherein the plurality of detectors in turn are in an imagining position to directly image the scintillator.

15. The radiation detection system of claim 1, in combination with a radiotherapy device, the combination comprising:
   a source of radiation;
   wherein the plurality of detectors are moveable to position each detector in turn in an imaging position to directly image the source of radiation.

16. The radiation detection system according to claim 1, further comprising or in combination with:
   a multi-leaf collimator
   wherein the plurality of detectors in turn are in an imaging position to image the position of one or more leaves of the multi-leaf collimator.

17. The radiation detection system according to claim 16, wherein when in the imaging position a particular detector of the plurality of detectors images light fluoresced or reflected from a marker on a leaf of the multi-leaf collimator.

18. The radiation detection system according to claim 1, wherein the detector is configured to image a patient during a radiotherapy procedure.

19. A method of operating a radiation detection system comprising a plurality of detectors included in a radiotherap device. the method comprising:
   imaging radiation using a first detector in an imaging position;
   receiving a command;
   upon receipt of the command, moving the first detector out of the imaging position and moving a second detector of the plurality of detectors into the imaging position, wherein the command is triggered by at least one of:
   a specified time interval;
   first detector having received a specified amount of radiation; and
   wherein the radiotherapy device produces an image, and wherein the command is triggered by a deterioration in quality of the image.

20. A non-transitory computer readable medium comprising computer executable instructions which, when executed by a processor, cause the processor to:
   image radiation using a first detector of a plurality of detectors included in a radiotherapy device, in an imaging position; receive a command;
   upon receipt of the command, move the first detector out of the imaging position and moving a second detector of the plurality of detectors into the imaging position, wherein the command is triggered by at least one of:
   a specified time interval; the first detector having received a specified amount of radiation;
   and wherein a radiotherapy device produces an image, and wherein the command is triggered by a deterioration in quality of the image.

* * * * *